US006492134B1

United States Patent
Aquin et al.

(10) Patent No.: US 6,492,134 B1
(45) Date of Patent: Dec. 10, 2002

(54) METHOD FOR PRODUCING POLYHYDROXYALKANOATES IN RECOMBINANT ORGANISMS

(75) Inventors: Stéphanie Aquin, Sainte-Foy (CA); Louis-P. Vézina, Neuville (CA)

(73) Assignees: Université Laval (CA); Her Majesty the Queen in right of Canada as represented by the Minister of Agriculture and Agri-Food Canada (CA)

( * ) Notice: Subject to any disclaimer, the term of this patent is extended or adjusted under 35 U.S.C. 154(b) by 0 days.

(21) Appl. No.: 09/526,098

(22) Filed: Mar. 15, 2000

Related U.S. Application Data

(60) Provisional application No. 60/124,417, filed on Mar. 15, 1999.

(51) Int. Cl.[7] .......................... C12P 1/00; C12N 15/87; C07H 21/02
(52) U.S. Cl. ...................... 435/41; 800/278; 536/23.1
(58) Field of Search ........................... 435/41; 800/298, 800/278; 536/23.1

(56) References Cited

U.S. PATENT DOCUMENTS

| | | | |
|---|---|---|---|
| 5,229,279 A | 7/1993 | Peoples et al. | |
| 5,245,023 A | 9/1993 | Peoples et al. | |
| 5,250,430 A | 10/1993 | Peoples et al. | |
| 5,298,421 A | 3/1994 | Davies et al. | |
| 5,480,794 A | 1/1996 | Peoples et al. | |
| 5,502,273 A | 3/1996 | Bright et al. | |
| 5,534,432 A | 7/1996 | Peoples et al. | |
| 5,610,041 A | 3/1997 | Somerville et al. | |
| 5,650,555 A | 7/1997 | Somerville et al. | |
| 5,663,063 A | 9/1997 | Peoples et al. | |
| 5,750,848 A | 5/1998 | Krüger et al. | |
| 5,801,027 A | 9/1998 | Bennett et al. | |
| 5,959,179 A | 9/1999 | Hinchee et al. | |
| 6,103,956 A * | 8/2000 | Srienc et al. | 800/289 |
| 6,265,202 B1 * | 7/2001 | Sherman et al. | |

FOREIGN PATENT DOCUMENTS

| | | |
|---|---|---|
| WO | WO 95/05472 | 2/1995 |
| WO | WO 98/00557 | 1/1998 |
| WO | WO 98/36078 | 8/1998 |
| WO | WO 99/00505 | 1/1999 |

OTHER PUBLICATIONS

Nawrath et al., PNAS 91 :12760–12764 (1994).*
Poirier et al., Bio/Technology 13: 142–150 (1995).*
Poirier et al., Science 256 : 520–523 (1992).*
Rehm et al., "A New Metabolic Link Between Fatty Acid de Novo Synthesis and Polyhydroxyalkanoic Acid Synthesis: The PHAG Gene From *Pseudomonas Putida* KT2440 Encodes a 3–Hydroxyacl–Acyl Carrier," *J. Biol. Chem.*, 273:24044–24051 (1998).
Hiltunen et al., "Peroxisomal Multifunctional β–Oxidation Protein of *Saccharomyces cerevisiae*," *J. Biol. Chem.* 267(10):6646–6653 (1992).
Fukui et al., "Expression and Characterization of (R)–Specific Enoyl Coenzyme A Hydratase Involved in Polyhydroxyalkanoate Bioxynthesis by *Aeromonas caviae*," *J. Bacteriol.* 180(3):667–673 (1998).
Williams et al., "Production of a Polyhydroxyalkanoate Biopolymer in Insect Cells with a Modified Eucaryotic Fatty Acid Synthase," *Appl. Environ. Microbiol.* 62(7):2540–2546 (1996).
Leaf et al., "*Saccharomyces cerevisiae* Expressing Bacterial Polyhydroxybutyrate Synthase Produces Poly–3–Hydroxybutyrate," *Microbiology* 142:1169–1180 (1996).
Mittendorf et al., "Synthesis of Medium–Chain–Length Polyhydroxyalkanoates in *Arabidopsis thaliana* Using Intermediates of Peroxisomal Fatty Acid β–Oxidation," *Proc. Natl. Acad. Sci. USA* 95:13397–13402 (1998).

* cited by examiner

*Primary Examiner*—Ethan C. Whisenant
(74) *Attorney, Agent, or Firm*—Nixon Peabody LLP

(57) ABSTRACT

The present biotechnological approach for the production of polyhydroxyalkanotes (PHAs) uses microbial systems. The high production costs makes them substantially more expensive than synthetic plastics. Engineering a novel pathway in eucaryotic cell systems is a beneficial alternative to the production of PHAs in bacteria. This pathway will initially produce free ($C_8$) fatty acids from the fatty acid synthetic pathway through the action of thioesterase, that will then add a CoA moiety to the free fatty acid through the action of an acyl-CoA synthetase, that will produce 3-ketoacyl-CoAs from the acyl-CoA through the action of a thiolase, that will produce R-(−)-OH-acyl-CoAs from the 3-keto acid CoAs through the action of a dehydrogenase isoform from yeasts. These R-(−)-3-OH-acyl-CoAs will finally be used as substrate for the PHA synthase reaction.

3 Claims, 15 Drawing Sheets

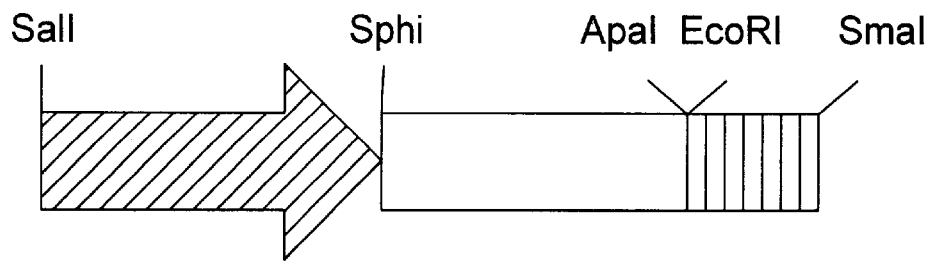
RbscK-DH-3'nc in pKitmus and pCambia 2300
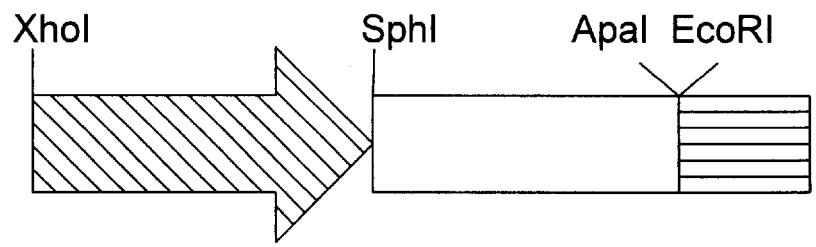
35S.C4PPDK.DH.3'nc in pUC18
- ▨ ALFALFA RUBISCO PROMOTER
- ▥ 3' NON-CODING REGION OF ALFALFA RUBISCO
- ▧ 35S-C4PPDK PROMOTER
- ▤ NOS
- ☐ 3-HYDROXYACYL-CoA DEHYDROGENASE
FIG. 4

```
GTTAACTACGTCAGGTGGCACTTTTCGGGGAAATGTGCGCGGAACCCCTATTTGTTTATT
TTTCTAAATACATTCAAATATGTATCCGCTCATGAGACAATAACCCTGATAAATGCTTCA
ATAATATTGAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCAACAGCGGTAA
GATCCTTGAGAGTTTTCGCCCCGAAGAACGTTCTCCAATGATGAGCACTTTTAAAGTTCT
GCTATGTGGCGCGGTATTATCCCGTGTTGACGCCGGGCAAGAGCAACTCGGTCGCCGCAT
ACACTATTCTCAGAATGACTTGGTTGAGTACTCACCAGTCACAGAAAAGCATCTTACGGA
TGGCATGACAGTAAGAGAATTATGCAGTGCTGCCATAACCATGAGTGATAACACTGCGGC
CAACTTACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCATACCAAA
CGACGAGCGTGACACCACGATGCCTGTAGCAATGGCAACAACGTTGCGCAAACTATTAAC
TGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATC
TGGAGCCGGTGAGCGTGGGTCTCGCGGTATCATTGCAGCACTGGGGCCAGATGGTAAGCC
CTCCCGTATCGTAGTTATCTACACGACGGGGAGTCAGGCAACTATGGATGAACGAAATAG
ACAGATCGCTGAGATAGGTGCCTCACTGATTAAGCATTGGTAACTGTCAGACCAAGTTTA
CTCATATATACTTTAGATTGATTTACCCCGGTTGATAATCAGAAAAGCCCCAAAAACAGG
AAGATTGTATAAGCAAATATTTAAATTGTAAACGTTAATATTTTGTTAAAATTCGCGTTA
AATTTTTGTTAAATCAGCTCATTTTTTAACCAATAGGCCGAAATCGGCAAAATCCCTTAT
AAATCAAAAGAATAGCCCGAGATAGGGTTGAGTGTTGTTCCAGTTTGGAACAAGAGTCCA
CTATTAAAGAACGTGGACTCCAACGTCAAAGGGCGAAAAACCGTCTATCAGGGCGATGGC
CCACTACGTGAACCATCACCCAAATCAAGTTTTTTGGGGTCGAGGTGCCGTAAAGCACTA
AATCGGAACCCTAAAGGGAGCCCCCGATTTAGAGCTTGACGGGGAAAGCGAACGTGGCGA
GAAAGGAAGGGAAGAAAGCGAAAGGAGCGGGCGCTAGGGCGCTGGCAAGTGTAGCGGTCA
CGCTGCGCGTAACCACCACACCCGCCGCGCTTAATGCGCCGCTACAGGGCGCGTAAAAGG
ATCTAGGTGAAGATCCTTTTTGATAATCTCATGACCAAAATCCCTTAACGTGAGTTTTCG
TTCCACTGAGCGTCAGACCCCGTAGAAAAGATCAAAGGATCTTCTTGAGATCCTTTTTTT
CTGCGCGTAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGCGCAGATA
CCAAATACTGTTCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGC
TGAACGGGGGGTTCGTGCACACAGCCCAGCTTGGAGCGAACGACCTACACCGAACTGAGA
TACCTACAGCGTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTG
TGATGCTCGTCAGGGGGCGGAGCCTATGGAAAAACGCCAGCAACGCGGCCTTTTTACGG
TTCCTGGCCTTTTGCTGGCCTTTTGCTCACATGTAATGTGAGTTAGCTCACTCATTAGGC
ACCCCAGGCTTTACACTTTATGCTTCCGGCTCGTATGTTGTGTGGAATTGTGAGCGGATA
ACAATTTCACACAGGAAACAGCTATGACCATGATTACGCCAAGCGTCGACctgcaggtca
acggatcaaatgattcaatatttggcttgatgaaattagagaaaatgaaaaattggattt
ctaagtttgattgttatttgagatagaaaggaaaaatctctaatctcttacgcaagac
ctgcctcaaccacttgataaactcttttgtctacgtattgaaaacaaaagaggcaaataa
acatctagccaaatgaaacaccaataatgctttaaacaaaatggaataattgcatcatca
attaatctttataagtgagaattttccctcctataataatgcgctaggtatcaatttcta
actctgaaatataaagcttcaagcgtgtgttatcaaaaatcaagcacagtaaaatcataa
```

FIGURE 5A gcagaatcattggtgatgctaatagttgatgtggaatcgaacaatgttcatattctgata
ccttgttggtgacaagtcaagacccttatagacttgaattttgtctgagttgatgatttc
agaagggggaatctagtatctaagtagatggtaaatttattttttccaattccagttgctt
ccattatgaacaaaccttattcttttaggctaatattgaggaacaaaagccacggaatat
tttttttatgtataacctaagaaaaagacaataataaaaataattaaaaactacaacaga
tgattttggacttgaatcgaattggattaatcttatacatgttgtcgataaggatactag
ttatatgaagaagagaatcaattgaaactttatttgtgctatatataatgatttatgata
tatggagagagggatggcagaatatgcaagtttggaatcaattctggacattcatggagg
gcgggtttatcatcgtgggtgtggtaggggtggctgaggttctagggctacccagtactt
ttatgatgttgttgtagtattttgaacaaatttgtttttaattttatgtttgaatattg
ggtttgtaacatatggataatttgtttttaattttatgttcgaaaattgtgttgttttg
atcatttttcattacaatatttatttatttattcacgaatgcatgtttatatcaacaaatt
atataatctgtatgtatcatagtgaaaacaaactctgttttttctttttgatacctttcaga
ttatataatttgaaatgtcataaaacagtttagattatataatctgaaatatgcgttttt
tacaccacattttgcatttgtgaggtgtttgacacttttcggattatataagtcaaatt
attttaagaagtttcggattatatatctgaaacatatgtttaactgacacatacacaaac
atctctagggtgatttgtcttccaatagtttttatactgtttggattatataatccgaat
caaggttaagaaaaaattagggcgctcgaaaaccaaatagggtgggaaaagtaatgacca
atattgattaccctataaggagccaaagcctgaaaaaagtaccatacatgattgatattt
gtggaggcattaatagtcacaaaactacacgtggcaatttatattggtggctaatgata
aggctagcacaaaaatttccattcctgtgtggttgatatggcagcaaagtttatcatatt
cacaaccaacaaaatggtattatgaagcattaccacaatttataagaccataatattgga
aataggaaaataaaaacattatatatagcaagtttgagtataagctttgcaattcaagca
gaagtacatcttactttactagtgaactaagtaagggagaaaaaaaatggcttcctctat
gatgtcctcttcagctgtgactacagttaaccgtgcctcttcggtacaatctggcgtggt
ggctccattcgttggactaaagtccatggctggcttcccagttacaaaggtcaacaaaga
cattacttccattgcaagcaatggtggaagagtaaact<u>GCATGC</u>taatgcctggaaattt
atccttcaaagatagagttgttgtaatcacggccgctggagggggcttaggtaaggtgta
tgcactagcttacgcaagcagaggtgcaaaagtggtcgtcaatgatctaggtggcacttt
gggtggttcaggacataactccaaagctgcagacttagtggtggatgagataaagaaagc
cggaggtatagctgtggcaaattacgactctgttaatgaaaatggagagaaaataattga
aacggctataaaagaattcggcagggttgatgtactaattaacaacgctggaatattgag
ggatgt<u>c</u>tcatttgcaaagatgacagaacgtgagtttgcatctgtggtagatgttcattt
gacaggtggctataagctatcgcgtgc<u>c</u>gcttggccttatatgcgctctcagaaatttgg
tagaatcattaacaccgcttcccctgccggtctatttggaaattttggtcaagctaatta
ttcagcagctaaaatgggcttagttggtttggcggaaaccctcgcgaaggagggtgccaa
atacaacattaatgttaattcaattgcgccattggctagatcacgtatgacagaaaacgt
gttaccaccacatatcttgaaacagttaggaccggaaaaaattgttcccttagtactcta
tttgacacacgaaagtacgaaagtgtcaaactccattttttgaactcgctgctggattctt
tggacagctcagatgggagaggtcttctggacaaattttcaatccagaccccaagacata
tactcctgaagcaattttaaataagtggaaggaaatcacagactatagggacaagccatt
taacaaaactcagcatccatatcaactctcggattataatgatttaatcaccaaagcaaa
aaaattacctcccaatgaacaaggctcagtgaaaatcaagtcgctttgcaacaaagtcgt
agtagttacgggtgcaggaggtggtcttgggaagtctcatgcaatctggtttgcacggta
cggtgcgaaggtagttgtaaatgacatcaaggatccttttcagttgttgaagaaataaa
taaactatatggtgaaggcacagccattccagattccatgatgtggtcaccgaagcgcc
tctcattatccaaactgcaataagtaagtttcagagagtagacatcttggtcaataacgc
tggtatttgcgtgacaaatctttttaaaaatgaaagatgaggaatggtttgctgtcct
gaaagtccaccttttttccacatttc<u>c</u>ttgtcaaaagcggtatggccaatatttactaa
acaaaagtctggatttattatcaatactacttctacctcaggaatttatggtaattttgg
acaggccaattatgccgctgcaaaagccgccatttta<u>g</u>ggttcagtaaaactattgcact
ggaaggtgccaagagaggaattattgttaatgttatcgctcctcatgcagaaacggctat
gacaaagactatattctcggagaaggaattatcaaaccactttgatgcatctcaagtctc

FIGURE 5B cccacttgttgttttgttggcatctgaagaactacaaaaatattctggaagaagggttat
tggccaattattcgaagttggcggtggttggtgtgggcaaaccagatggcaaagaagttc
cggttatgtttctattaaagagactattgaaccggaagaaattaaagaaaattggaacca
catcactgatttcagtcgcaacactatcaacccgtaaGGGCCCctcgaggagctcGAATT
Catttgagaatttactatctgccattgaaggaacattttttctctccatttgttctgtt
tgtaatttccttttctttttaaaggaaatgtctccagtgttttttcggtatttgctttcg
gattttgaaatgcaaatagatggataagagttaattaatgaaatgatactttattcatt
ctcaaattagtttcattaatggatatataaagataaagtaataactgcgcctatgcttcc
tttgcattgaagcaactgaactttacctaattgaaatatctttacccttggcaactaaat
gagtgaatgatgaattggtcgtcgaaattgtgagcattttgtcaaaatagtcctgaaat
atgctatttgagaaataaatctgaactgtacgcatcagtaCCCGGGTGAGTCGTATTACG
GACTGGCCGTCGTTTTACAACGTCGTGACTGGGAAAACCCTGGCGTTACCCAACTTAATC
GCCTTGCAGCACATCCCCCTTTCGCCAGCTGGCGTAATAGCGAAGAGGCCCGCACCGATC
GCCCTTCCCAACAGTTGCGCAGCCTGAATGGCGAATGGCGCTTCGCTTGGTAATAAAGCC
CGCTTCGGCGGGCTTTTTTT

FIGURE 5C

```
TCTTCCGCTTCCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTGGCG
TTTTTCCATAGGCTCCGCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTAGGTCGTTCGC
TCCAAGCTGGGCTGTGTGCACGAACCCCCGTTCAGCCCGACCGCTGCGCCTTATCCGGT
AACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGTGG
CCTAACTACGGCTACACTAGAAGGACAGTATTTGGTATCTGCGCTCTGCTGAAGCCAGTT
ACCTTCGGAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCT
TTGATCTTTTCTACGGGGTCTGACGCTCAGTGGAACGAAAACTCACGTTAAGGGATTTTG
GTCATGAGATTATCAAAAGGATCTTCACCTAGATCCTTTTAAATTAAAAATGAAGTTTT
AAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATACCG
CGAGACCCACGCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACA
GGCATCGTGGTGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCA
ACCAAGTCATTCTGAGAATAGTGTATGCGGCGACCGAGTTGCTCTTGCCCGGCGTCAATA
CGGGATAATACCGCGCCACATAGCAGAACTTTAAAAGTGCTCATCATTGGAAAACGTTCT
TCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAATACTC
ATACTCTTCCTTTTTCAATATTATTGAAGCATTTATCAGGGTTATTGTCTCATGAGCGGA
TACATATTTGAATGTATTTAGAAAAATAAACAAATAGGGGTTCCGCGCACATTTCCCCGA
AAAGTGCCACCTGACGTCTAAGAAACCATTATTATCATGACATTAACCTATAAAAATAGG
CGTATCACGAGGCCCTTTCGTCTCGCGCGTTTCGGTGATGACGGTGAAAACCTCTGACAC
ATGCAGCTCCCGGAGACGGTCACAGCTTGTCTGTAAGCGGATGCCGGGAGCAGACAAGCC
CGTCAGGGCGCGTCAGCGGGTGTTGGCGGGTGTCGGGCTGGCTTAACTATGCGGCATCA
GAGCAGATTGTACTGAGAGTGCACCATATGCGGTGTGAAATACCGCACAGATGCGTAAGG
AGAAAATACCGCATCAGGCGCCATTCGCCATTCAGGCTGCGCAACTGTTGGGAAGGGCGA
TCGGTGCGGGCCTCTTCGCTATTACGCCAGCTGGCGAAAGGGGGATGTGCTGCAAGGCGA
TTAAGTTGGGTAACGCCAGGGTTTTCCCAGTCACGACGTTGTAAAACGACGGCCAGTGCC
AAGCTCTCGAGAAGCTTACTCCAAGAATATCAAAGATACAGTCTCAGAAGACCAAAGGGC
TATTGAGACTTTTCAACAAAGGGTAATATCGGGAAACCTCCTCGGATTCCATTGCCCAGC
TATCTGTCACTTCATCAAAAGGACAGTAGAAAGGAAGGTGGCACCTACAAATGCCATCA
TTGCGATAAAGGAAAGGCTATCGTTCAAGATGCCTCTGCCGACAGTGGTCCCAAAGATGG
ACCCCCACCCACAAGGAGCATCGTGGAAAAGAAGACGTTCCAACCACGTCTTCAAAGCA
AGTGGATTGATGTGATATCTCCACTGACGTAAGGATGACGCACAATCCCACTATCCTTC
GCCCCAAGCTTGGGCCCAAGCTTGGGTCGCGCCCCACGGATGGTATAAGAATAAAGGCAT
TCCGCGTGCAGGATTCACCCGTTCGCCTCTCACCTTTTCGCTGTACTCTCTCGCCACACA
CACCCCCTCTCCAGCTCCGTTGGAGCTCCGGACAGCAGCAGGCGCGGGGCGGTCACGTAG
```

FIGURE 5D

```
TAAGCAGCTCTCGGCTCCCTCTCCCCTTGCTCCGTGGATCGGCATGCTAATGCCTGGAAA
TTTATCCTTCAAAGATAGAGTTGTTGTAATCACGGGCGCTGGAGGGGGCTTAGGTAAGGT
GTATGCACTAGCTTACGCAAGCAGAGGTGCAAAAGTGGTCGTCAATGATCTAGGTGGCAC
TTTGGGTGGTTCAGGACATAACTCCAAAGCTGCAGACTTAGTGGTGGATGAGATAAAGAA
AGCCGGAGGTATAGCTGTGGCAAATTACGACTCTGTTAATGAAAATGGAGAGAAAATAAT
TGAAACGGCTATAAAGAATTCGGCAGGGTTGATGTACTAATTAACAACGCTGGAATATT
GAGGGATGTCTCATTTGCAAAGATGACAGAACGTGAGTTTGCATCTGTGGTAGATGTTCA
TTTGACAGGTGGCTATAAGCTATCGCGTGCCGCTTGGCCTTATATGCGCTCTCAGAAATT
TGGTAGAATCATTAACACCGCTTCCCCTGCCGGTCTATTTGGAAATTTTGGTCAAGCTAA
TTATTCAGCAGCTAAAATGGGCTTAGTTGGTTTGGCGGAAACCCTCGCGAAGGAGGGTGC
CAAATACAACATTAATGTTAATTCAATTGCGCCATTGGCTAGATCACGTATGACAGAAAA
CGTGTTACCACCACATATCTTGAAACAGTTAGGACCGGAAAAAATTGTTCCCTTAGTACT
CTATTTGACACACGAAAGTACGAAGTGTCAAACTCCATTTTGAACTCGCTGCTGGATT
CTTTGGACAGCTCAGATGGGAGAGGTCTTCTGGACAAATTTTCAATCCAGACCCCAAGAC
ATATACTCCTGAAGCAATTTTAAATAAGTGGAAGGAAATCACAGACTATAGGGACAAGCC
ATTAACAAAACTCAGCATCCATATCAACTCTCGGATTATAATGATTTAATCACCAAAGC
AAAAAAATTACCTCCCAATGAACAAGGCTCAGTGAAAATCAAGTCGCTTTGCAACAAAGT
CGTAGTAGTTACGGGTGCAGGAGGTGGTCTTGGGAAGTCTCATGCAATCTGGTTTGCACG
GTACGGTGCGAAGGTAGTTGTAAATGACATCAAGGATCCTTTTTCAGTTGTTGAAGAAAT
AAATAAACTATATGGTGAAGGCACAGCCATTCCAGATTCCCATGATGTGGTCACCGAAGC
GCCTCTCATTATCCAAACTGCAATAAGTAAGTTTCAGAGAGTAGACATCTTGGTCAATAA
CGCTGGTATTTTGCGTGACAAATCTTTTTTAAAAATGAAAGATGAGGAATGGTTTGCTGT
CCTGAAAGTCCACCTTTTTTCCACATTTTCCTTGTCAAAAGCGGTATGGCCAATATTTAC
TAAACAAAAGTCTGGATTTATTATCAATACTACTTCTACCTCAGGAATTTATGGTAATTT
TGGACAGGCCAATTATGCCGCTGCAAAAGCCGCCATTTTAGGGTTCAGTAAAACTATTGC
ACTGGAAGGTGCCAAGAGAGGAATTATTGTTAATGTTATCGCTCCTCATGCAGAAACGGC
TATGACAAAGACTATATTCTCGGAGAAGGAATTATCAAACCACTTTGATGCATCTCAAGT
CTCCCCACTTGTTGTTTTGTTGGCATCTGAAGAACTACAAAAATATTCTGGAAGAAGGGT
TATTGGCCAATTATTCGAAGTTGGCGGTGGTTGGTGTGGGCAAACCAGATGGCAAAGAAG
TTCCGGTTATGTTTCTATTAAAGAGACTATTGAACCGGAAGAAATTAAAGAAAATTGGAA
CCACATCACTGATTTCAGTCGCAACACTATCAACCCGTAAGGGCCCCTCGAGGAGCTCGA
ATTCATTTGAGAATTTACTATCTGCCATTGAAGGAACATTTTTTTCTCTCCATTTGTTCT
GTTTGTAATTTCCTTTTCTTTTTAAAGGAAATGTCTCCAGTGTTTTTTCGGTATTTGCTT
TCGGATTTTGAAATGCAAATAGATGGATAAGAGTTAATTAATGAAATGATACTTTTATTC
ATTCTCAAATTAGTTTCATTAATGGATATATAAAGATAAAGTAATAACTGCGCCTATGCT
TCCTTTGCATTGAAGCAACTGAACTTTACCTAATTGAAATATCTTTACCCTTGGCAACTA
AATGAGTGAATGATGAATTGGTCGTCGAAATTGTGAGCATTTTGTCAAAATAGTCCTGA
AATATGCTATTTGAGAAATAAATCTGAACTGTACGCATCAGTACCCAATTCGTAATCATG
GTCATAGCTGTTTCCTGTGTGAAATTGTTATCCGCTCACAATTCCACACAACATACGAGC
CGGAAGCATAAAGTGTAAAGCCTGGGGTGCCTAATGAGTGAGCTAACTCACATTAATTGC
GTTGCGCTCACTGCCCGCTTTCCAGTCGGGAAACCTGTCGTGCCAGCTGCATTAATGAAT
CGGCCAACGCGCGGGGAGAGGCGGTTTGCGTATTGGGCGC
```

FIGURE 5E

CACATACAAATGGACGAACGGATAAACCTTTTCACGCCCTTTTAAATATCCGTTATTCTA
ATAAACGCTCTTTTCTCTTAGGTTTACCCGCCAATATATCCTGTCAAACACTGATAGTTT
AAACTGAAGGCGGGAAACGACAATCTGATCCAAGCTCAAGCTGCTCTAGCATTCGCCATT
CAGGCTGCGCAACTGTTGGGAAGGGCGATCGGTGCGGGCCTCTTCGCTATTACGCCAGCT
GGCGAAAGGGGGATGTGCTGCAAGGCGATTAAGTTGGGTAACGCCAGGGTTTTCCCAGTC
ACGACGTTGTAAAACGACGGCCAGTGCCAAGCTTGCATGCCTGCAG<u>GTCGAC</u>ctgcaggt
caacggatcaaatgattcaatatttggcttgatgaaattagagaaaatgaaaaattggat
ttctaagtttgattgttattttgagatagaaaaggaaaaatctctaatctcttacgcaag
acctgcctcaaccacttgataaactcttttgtctacgtattgaaaacaaaagaggcaaat
aaacatctagccaaatgaaacaccaataatgctttaaacaaaatggataattgcatcat
caattaatctttataagtgagaattttccctcctataataatgcgctaggtatcaatttt
caactctgaaatataaagcttcaagcgtgtgttatcaaaatcaagcacagtaaaatcat
aagcagaatcattggtgatgctaatagttgatgtggaatcgaacaatgttcatattctga
taccttgttggtgacaagtcaagacccttatagacttgaattttgtctgagttgatgatt
tcagaaggggaatctagtatctaagtagatggtaaatttattttttccaattccagttgc
ttccattatgaacaaaccttattcttttaggctaatattgaggaacaaaagccacggaat
atttttttatgtataacctaagaaaagacaataataaaaataattaaaaactacaaca
gatgatttggacttgaatcgaattggattaatcttatacatgttgtcgataaggatact
agttatatgaagaagagaatcaattgaaactttatttgtgctatatataatgatttatga
tatatggagagagggatggcagaatatgcaagtttggaatcaattctggacattcatgga
gggcgggtttatcatcgtgggtgtggtaggggtggctgaggttctagggctacccagtac
ttttatgatgttgttgtagtattttgaacaaatttgttttttaattttatgtttgaatat
tgggtttgtaacatatggataatttgttttaattttatgttcgaaaattgtgttgttttt
tgatcatttcattacaatatttatttatttattcacgaatgcatgtttatatcaacaaa
ttatataatctgtatgtatcatagtgaaaacaaactctgtttttcttttgatacctttca
gattatataatttgaaatgtcataaaacagtttagattatataatctgaaatatgcgttt
tttacaccacattttgcattttgtgaggtgtttgacacttttcggattatataagtcaaa
ttattttaagaagtttcggattatatatctgaaacatatgtttaactgacacatacacaa
acatctctagggtgatttgtcttccaatagttttatactgtttggattatataatccga
atcaaggttaagaaaaattagggcgctcgaaaaccaaatagggtgggaaaagtaatgac
caatattgattaccctataaggagccaaagcctgaaaaaagtaccatacatgattgatat
ttgtggaggcattaatagtcacaaaactacacgtggcaatttatattggtggctaatga
taaggctagcacaaaaatttccattcctgtgtggttgatatggcagcaaagtttatcata
ttcacaaccaacaaatggtattatgaagcattaccacaatttataagaccataatattg
gaaataggaaaataaaaacattatatatagcaagtttgagtataagctttgcaattcaag
cagaagtacatcttactttactagtgaactaagtaagggagaaaaaaaa<u>atg</u>gcttcctct
atgatgtcctcttcagctgtgactacagttaaccgtgcctcttcggtacaatctggcgtg
gtggctccattcgttggactaaagtccatggctggcttccagttacaaaggtcaacaaa
gacattacttccattgcaagcaatggtggaagagtaaact<u>GCATGC</u>taatgcctggaaat
ttatccttcaaagatagagttgttgtaatcacggccgctggaggggcttaggtaaggtg
tatgcactagcttacgcaagcagaggtgcaaagtggtcgtcaatgatctaggtggcact
ttgggtggttcaggacataactccaaagctgcagacttagtggtggatgagataaagaaa
gccggaggtatagctgtggcaaattacgactctgttaatgaaaatggagagaaaataatt
gaaacggctataaagaattcggcagggttgatgtactaattaacaacgctggaatattg
agggatgtctcatttgcaaagatgacagaacgtgagtttgcatctgtggtagatgttcat
ttgacaggtggctataagctatcgcgtgccgcttggccttatatgcgctctcagaaattt
ggtagaatcattaacaccgcttccctgccggtctatttggaaattttggtcaagctaat
tattcagcagctaaatgggcttagttggtttggcggaaaccctcgcgaaggagggtgcc

FIGURE 5F

```
aaatacaacattaatgttaattcaattgcgccattggctagatcacgtatgacagaaaac
gtgttaccaccacatatcttgaaacagttaggaccggaaaaaattgttcccttagtactc
tatttgacacacgaaagtacgaaagtgtcaaactccattttttgaactcgctgctggattc
tttggacagctcagatgggagaggtcttctggacaaattttcaatccagacccaagaca
tatactcctgaagcaattttaaataagtggaaggaaatcacagactatagggacaagcca
tttaacaaaactcagcatccatatcaactctcggattataatgatttaatcaccaaagca
aaaaaattacctcccaatgaacaaggctcagtgaaaatcaagtcgctttgcaacaaagtc
gtagtagttacgggtgcaggaggtggtcttgggaagtctcatgcaatctggtttgcacgg
tacggtgcgaaggtagttgtaaatgacatcaaggatccttttcagttgttgaagaaata
aataaactatatggtgaaggcacagccattccagattccatgatgtggtcaccgaagcg
cctctcattatccaaactgcaataagtaagtttcagagagtagacatcttggtcaataac
gctggtattttgcgtgacaaatcttttttaaaaatgaaagatgaggaatggtttgctgtc
ctgaaagtccaccttttttccacattttcattgtcaaaagcggtatggccaatatttact
aaacaaaagtctggatttattatcaatactacttctacctcaggaatttatggtaatttt
ggacaggccaattatgccgctgcaaaagccgccatttagggttcagtaaaactattgca
ctggaaggtgccaagagaggaattattgttaatgttatcgctcctcatgcagaaacggct
atgacaaagactatattctcggagaaggaattatcaaaccactttgatgcatctcaagtc
tccccacttgttgttttgttggcatctgaagaactacaaaaatattctggaagaagggtt
attggccaattattcgaagttggcggtggttggtgtgggcaaaccagatggcaaagaagt
tccggttatgtttctattaaagagactattgaaccggaagaaattaaagaaaattggaac
cacatcactgatttcagtcgcaacactatcaacccgtaaGGGCCCctcgaggagctcGAA
TTCatttgagaatttactatctgccattgaaggaacatttttttctctccatttgttctg
tttgtaatttccttttcttttaaaggaaatgtctccagtgttttttcggtatttgcttt
cggattttgaaatgcaaatagatggataagagttaattaatgaaatgatactttattca
ttctcaaattagtttcattaatggatatataaagataaagtaataactgcgcctatgctt
cctttgcattgaagcaactgaactttacctaattgaaatatctttaccttggcaactaa
atgagtgaatgatgaattggtcgtcgaaattgtgagcattttgtcaaaatagtcctgaa
atatgctatttgagaaataaatctgaactgtacgcatcagtaCCCGGGTACCGAGCTCGA
ATTCGTAATCATGGTCATAGCTGTTTCCTGTGTGAAATTGTTATCCGCTCACAATTCCAC
ACAACATACGAGCCGGAAGCATAAAGTGTAAAGCCTGGGGTGCCTAATGAGTGAGCTAAC
TCACATTAATTGCGTTGCGCTCACTGCCCGCTTTCCAGTCGGGAAACCTGTCGTGCCAGC
TGCATTAATGAATCGGCCAACGCGCGGGGAGAGGCGGTTTGCGTATTGGCTAGAGCAGCT
TGCCAACATGGTGGAGCACGACACTCTCGTCTACTCCAAGAATATCAAAGATACAGTCTC
AGAAGACCAAAGGGCTATTGAGACTTTTCAACAAAGGGTAATATCGGGAAACCTCCTCGG
ATTCCATTGCCCAGCTATCTGTCACTTCATCAAAAGGACAGTAGAAAAGGAAGGTGGCAC
CTACAAATGCCATCATTGCGATAAAGGAAAGGCTATCGTTCAAGATGCCTCTGCCGACAG
TGGTCCCAAAGATGGACCCCCACCCACGAGGAGCATCGTGGAAAAGAAGACGTTCCAAC
CACGTCTTCAAAGCAAGTGGATTGATGTGATAACATGGTGGAGCACGACACTCTCGTCTA
CTCCAAGAATATCAAAGATACAGTCTCAGAAGACCAAAGGGCTATTGAGACTTTTCAACA
AAGGGTAATATCGGGAAACCTCCTCGGATTCCATTGCCCAGCTATCTGTCACTTCATCAA
AAGGACAGTAGAAAAGGAAGGTGGCACCTACAAATGCCATCATTGCGATAAAGGAAAGGC
TATCGTTCAAGATGCCTCTGCCGACAGTGGTCCCAAAGATGGACCCCCACCCACGAGGAG
CATCGTGGAAAAGAAGACGTTCCAACCACGTCTTCAAAGCAAGTGGATTGATGTGATAT
CTCCACTGACGTAAGGGATGACGCACAATCCCACTATCCTTCGCAAGACCTTCCTCTATA
TAAGGAAGTTCATTTCATTTGGAGAGGACACGCTGAAATCACCAGTCTCTCTCTACAAAT
CTATCTCTCTCGAGCTTTCGCAGATCTGTCGATCGACCATGGGGATTGAACAAGATGGAT
TGCACGCAGGTTCTCCGGCCGCTTGGGTGGAGAGGCTATTCGGCTATGACTGGGCACAAC
AGACAATCGGCTGCTCTGATGCCGCCGTGTTCCGGCTGTCAGCGCAGGGGCGCCCGGTTC
TTTTTGTCAAGACCGACCTGTCCGGTGCCCTGAATGAACTCCAGGACGAGGCAGCGCGGC
TATCGTGGCTGGCCACGACGGGCGTTCCTTGCGCAGCTGTGCTCGACGTTGTCACTGAAG
CGGGAAGGGACTGGCTGCTATTGGGCGAAGTGCCGGGGCAGGATCTCCTGTCATCTCACC
TTGCTCCTGCCGAGAAAGTATCCATCATGGCTGATGCAATGCGGCGGCTGCATACGCTTG
ATCCGGCTACCTGCCCATTCGACCACCAAGCGAAACATCGCATCGAGCGAGCACGTACTC
GGATGGAAGCCGGTCTTGTCGATCAGGATGATCTGGACGAAGAGCATCAGGGGCTCGCGC
```

FIGURE 5G

```
CAGCCGAACTGTTCGCCAGGCTCAAGGCGCGCATGCCCGACGGCGAGGATCTCGTCGTGA
CACATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTG
ATATTGCTGAAGAGCTTGGCGGCGAATGGGCTGACCGCTTCCTCGTGCTTTACGGTATCG
CCGCTCCCGATTCGCAGCGCATCGCCTTCTATCGCCTTCTTGACGAGTTCTTCTGAGCGG
GACTCTGGGGTTCGGATCGATCCTCTAGCTAGAGTCGATCGACAAGCTCGAGTTTCTCCA
TAATAATGTGTGAGTAGTTCCCAGATAAGGGAATTAGGGTTCCTATAGGGTTTCGCTCAT
GTGTTGAGCATATAAGAAACCCTTAGTATGTATTTGTATTTGTAAAATACTTCTATCAAT
AAAATTTCTAATTCCTAAAACCAAAATCCAGTACTAAAATCCAGATCCCCGAATTAATT
CGGCGTTAATTCAGTACATTAAAAACGTCCGCAATGTGTTATTAAGTTGTCTAAGCGTCA
ATTTGTTTACACCACAATATATCCTGCCACCAGCCAGCCAACAGCTCCCGACCGGCAGC
TCGGCACAAAATCACCACTCGATACAGGCAGCCCATCAGTCCGGGACGGCGTCAGCGGGA
GAGCCGTTGTAAGCGGCAGACTTTGCTCATGTTACCGATGCTATTCGGAAGAACGGCAA
CTAAGCTGCCGGGTTTGAAACACGGATGATCTCGCGGAGGGTAGCATGTTGATTGTAACG
ATGACAGAGCGTTGCTGCCTGTGATCACCGCGGTTTCAAAATCGGCTCCGTCGATACTAT
GTTATACGCCAACTTTGAAAACAACTTTGAAAAAGCTGTTTTCTGGTATTTAAGGTTTTA
GAATGCAAGGAACAGTGAATTGGAGTTCGTCTTGTTATAATTAGCTTCTTGGGGTATCTT
TAAATACTGTAGAAAAGAGGAAGGAAATAATAAATGGCTAAAATGAGAATATCACCGGAA
TTGAAAAAACTGATCGAAAAATACCGCTGCGTAAAAGATACGGAAGGAATGTCTCCTGCT
AAGGTATATAAGCTGGTGGGAGAAAATGAAAACCTATATTTAAAAATGACGGACAGCCGG
TATAAAGGGACCACCTATGATGTGGAACGGGAAAAGGACATGATGCTATGGCTGGAAGGA
AAGCTGCCTGTTCCAAAGGTCCTGCACTTTGAACGGCATGATGGCTGGAGCAATCTGCTC
ATGAGTGAGGCCGATGGCGTCCTTTGCTCGGAAGAGTATGAAGATGAACAAAGCCCTGAA
AAGATTATCGAGCTGTATGCGGAGTGCATCAGGCTCTTTCACTCCATCGACATATCGGAT
TGTCCCTATACGAATAGCTTAGACAGCCGCTTAGCCGAATTGGATTACTTACTGAATAAC
GATCTGGCCGATGTGGATTGCGAAAACTGGGAAGAAGACACTCCATTTAAAGATCCGCGC
GAGCTGTATGATTTTTTAAAGACGGAAAAGCCCGAAGAGGAACTTGTCTTTTCCCACGGC
GACCTGGGAGACAGCAACATCTTTGTGAAAGATGGCAAAGTAAGTGGCTTTATTGATCTT
GGGAGAAGCGGCAGGGCGGACAAGTGGTATGACATTGCCTTCTGCGTCCGGTCGATCAGG
GAGGATATCGGGGAAGAACAGTATGTCGAGCTATTTTTGACTTACTGGGGATCAAGCCT
GATTGGGAGAAAATAAAATATTATATTTACTGGATGAATTGTTTTAGTACCTAGAATGC
ATGACCAAAATCCCTTAACGTGAGTTTTCGTTCCACTGAGCGTCAGACCCCGTAGAAAAG
ATCAAAGGATCTTCTTGAGATCCTTTTTTCTGCGCGTAATCTGCTGCTTGCAAACAAAA
AAACCACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGCCGTAG
TTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGC
TTGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGGA
GAGCGCACGAGGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGCGGAGCCTATGG
AAAAACGCCAGCAACGCGGCCTTTTTACGGTTCCTGGCCTTTTGCTGGCCTTTTGCTCAC
ATGTTCTTTCCTGCGTTATCCCCTGATTCTGTGGATAACCGTATTACCGCCTTTGAGTGA
GCTGATACCGCTCGCCGCAGCCGAACGACCGAGCGCAGCGAGTCAGTGAGCGAGGAAGCG
GAAGAGCGCCTGATGCGGTATTTTCTCCTTACGCATCTGTGCGGTATTTCACACCGCATA
TGGTGCACTCTCAGTACAATCTGCTCTGATGCCGCATAGTTAAGCCAGTATACACTCCGC
TATCGCTACGTGACTGGGTCATGGCTGCGCCCCGACACCCGCCAACACCCGCTGACGCGC
CCTGACGGGCTTGTCTGCTCCCGGCATCCGCTTACAGACAAGCTGTGACCGTCTCCGGGA
GCTGCATGTGTCAGAGGTTTTCACCGTCATCACCGAAACGCGCGAGGCAGGGTGCCTTGA
TGTGGGCGCCGGCGGTCGAGTGGCGACGGCGCGGCTTGTCCGCGCCTGGTAGATTGCCT
GGCCGTAGGCCAGCCATTTTTGAGCGGCCAGCGGCCGCGATAGGCCGACGCGAAGCGGCG
GGGCGTAGGGAGCGCAGCGACCGAAGGGTAGGCGCTTTTGCAGCTCTTCGGCTGTGCGC
TGGCCAGACAGTTATGCACAGGCCAGGCGGGTTTTAAGAGTTTTAATAAGTTTTAAAGAG
```

FIGURE 5H

```
TTTTAGGCGGAAAAATCGCCTTTTTTCTCTTTTATATCAGTCACTTACATGTGTGACCGG
TTCCCAATGTACGGCTTTGGGTTCCCAATGTACGGGTTCCGGTTCCCAATGTACGGCTTT
GGGTTCCCAATGTACGTGCTATCCACAGGAAAGAGACCTTTTCGACCTTTTTCCCCTGCT
AGGGCAATTTGCCCTAGCATCTGCTCCGTACATTAGGAACCGGCGGATGCTTCGCCCTCG
ATCAGGTTGCGGTAGCGCATGACTAGGATCGGGCCAGCCTGCCCCGCCTCCTCCTTCAAA
TCGTACTCCGGCAGGTCATTTGACCCGATCAGCTTGCGCACGGTGAAACAGAACTTCTTG
AACTCTCCGGCGCTGCCACTGCGTTCGTAGATCGTCTTGAACAACCATCTGGCTTCTGCC
TTGCCTGCGGCGCGGCGTGCCAGGCGGTAGAGAAAACGGCCGATGCCGGGATCGATCAAA
AAGTAATCGGGGTGAACCGTCAGCACGTCCGGGTTCTTGCCTTCTGTGATCTCGCGGTAC
ATCCAATCAGCTAGCTCGATCTCGATGTACTCCGGCCGCCGGTTTCGCTCTTTACGATC
TTGTAGCGGCTAATCAAGGCTTCACCCTCGGATACCGTCACCAGGCGGCCGTTCTTGGCC
TTCTTCGTACGCTGCATGGCAACGTGCGTGGTGTTTAACCGAATGCAGGTTTCTACCAGG
TCGTCTTTCTGCTTTCCGCCATCGGCTCGCCGGCAGAACTTGAGTACGTCCGCAACGTGT
GGACGGAACACGCGGCCGGGCTTGTCTCCCTTCCCTTCCCGGTATCGGTTCATGGATTCG
GTTAGATGGGAAACCGCCATCAGTACCAGGTCGTAATCCCACACACTGGCCATGCCGGCC
GGCCCTGCGGAAACCTCTACGTGCCCGTCTGGAAGCTCGTAGCGGATCACCTCGCCAGCT
CGTCGGTCACGCTTCGACAGACGGAAAACGGCCACGTCCATGATGCTGCGACTATCGCGG
GTGCCCACGTCATAGAGCATCGGAACGAAAAAATCTGGTTGCTCGTCGCCCTTGGGCGGC
TTCCTAATCGACGGCGCACCGGCTGCCGGCGGTTGCCGGGATTCTTTGCGGATTCGATCA
GCGGCCGCTTGCCACGATTCACCGGGGCGTGCTTCTGCCTCGATGCGTTGCCGCTGGGCG
GCCTGCGCGGCCTTCAACTTCTCCACCAGGTCATCACCCAGCGCCGCGCCGATTTGTACC
GGGCCGGATGGTTTGCGACCGTCACGCCGATTCCTCGGGCTTGGGGGTTCCAGTGCCATT
GCAGGGCCGGCAGACAACCCAGCCGCTTACGCCTGGCCAACCGCCCGTTCCTCCACACAT
GGGGCATTCCACGGCGTCGGTGCCTGGTTGTTCTTGATTTTCCATGCCGCCTCCTTTAGC
CGCTAAAATTCATCTACTCATTTATTCATTTGCTCATTTACTCTGGTAGCTGCGCGATGT
ATTCAGATAGCAGCTCGGTAATGGTCTTGCCTTGGCGTACCGCGTACATCTTCAGCTTGG
TGTGATCCTCCGCCGGCAACTGAAAGTTGACCCGCTTCATGGCTGGCGTGTCTGCCAGGC
TGGCCAACGTTGCAGCCTTGCTGCTGCGTGCGCTCGGACGGCCGGCACTTAGCGTGTTTG
TGCTTTTGCTCATTTTCTCTTTACCTCATTAACTCAAATGAGTTTTGATTTAATTTCAGC
GGCCAGCGCCTGGACCTCGCGGGCAGCGTCGCCCTCGGGTTCTGATTCAAGAACGGTTGT
GCCGGCGGCGGCAGTGCCTGGGTAGCTCACGCGCTGCGTGATACGGGACTCAAGAATGGG
CAGCTCGTACCCGGCCAGCGCCTCGGCAACCTCACCGCCGATGCGCGTGCCTTTGATCGC
CCGCGACACGACAAAGGCCGCTTGTAGCCTTCCATCCGTGACCTCAATGCGCTGCTTAAC
CAGCTCCACCAGGTCGGCGGTGGCCCATATGTCGTAAGGGCTTGGCTGCACCGGAATCAG
CACGAAGTCGGCTGCCTTGATCGCGGACACAGCCAAGTCCGCCGCCTGGGCGCTCCGTC
GATCACTACGAAGTCGCGCCGGCCGATGGCCTTCACGTCGCGGTCAATCGTCGGGCGGTC
GATGCCGACAACGGTTAGCGGTTGATCTTCCCGCACGGCCGCCCAATCGCGGGCACTGCC
CTGGGGATCGGAATCGACTAACAGAACATCGGCCCCGGCGAGTTGCAGGGCGCGGGCTAG
ATGGGTTGCGATGGTCGTCTTGCCTGACCCGCCTTTCTGGTTAAGTACAGCGATAACCTT
CATGCGTTCCCCTTGCGTATTTGTTTATTTACTCATCGCATCATATACGCAGCGACCGCA
TGACGCAAGCTGTTTTACTCAAATACACATCACCTTTTTAGACGGCGGCGCTCGGTTTCT
TCAGCGGCCAAGCTGGCCGGCCAGGCCGCCAGCTTGGCATCAGACAAACCGGCCAGGATT
TCATGCAGCCGCACGGTTGAGACGTGCGCGGGCGGCTCGAACACGTACCCGGCCGCGATC
ATCTCCGCCTCGATCTCTTCGGTAATGAAAAACGGTTCGTCCTGGCCGTCCTGGTGCGGT
TTCATGCTTGTTCCTCTTGGCGTTCATTCTCGGCGGCCGCCAGGGCGTCGGCCTCGGTCA
ATGCGTCCTCACGGAAGGCACCGCGCCGCCTGGCCTCGGTGGGCGTCACTTCCTCGCTGC
GCTCAAGTGCGCGGTACAGGGTCGAGCGATGCACGCGTGCGCGATCTGTGCCGGGGTGAGGG
TAGGGCGGGGCCAAACTTCACGCCTCGGGCCTTGGCGGCCTCGCGCCCGCTCCGGGTGC
GGTCGATGATTAGGGAACGCTCGAACTCGGCAATGCCGGCGAACACGGTCAACACCATGC
GGCCGGCCGGCGTGGTGGTGTCGGCCCACGGCTCTGCCAGGCTACGCAGGCCCGCGCCGG
CCTCCTGGATGCGCTCGGCAATGTCCAGTAGGTCGCGGGTGCTGCGGGCCAGGCGGTCTA
GCCTGGTCACTGTCACAACGTCGCCAGGGCGTAGGTGGTCAAGCATCCTGGCCAGCTCCG
GGCGGTCGCGCCTGGTGCCGGTGATCTTCTCGGAAAACAGCTTGGTGCAGCCGGCCGCGT
```

FIGURE 5I

```
GCAGTTCGGCCCGTTGGTTGGTCAAGTCCTGGTCGTCGGTGCTGACGCGGGCATAGCCCA
GCAGGCCAGCGGCGGCGCTCTTGTTCATGGCGTAATGTCTCCGGTTCTAGTCGCAAGTAT
TCTACTTTATGCGACTAAAACACGCGACAAGAAAACGCCAGGAAAAGGGCAGGGCGGCAG
CCTGTCGCGTAACTTAGGACTTGTGCGACATGTCGTTTTCAGAAGACGGCTGCACTGAAC
GTCAGAAGCCGACTGCACTATAGCAGCGGAGGGGTTGGATCAAAGTACTTTGATCCCGAG
GGGAACCCTGTGGTTGGCATG
```

FIGURE 5J

METHOD FOR PRODUCING POLYHYDROXYALKANOATES IN RECOMBINANT ORGANISMS

The present application claims the benefit of U.S. Provisional Patent Application Ser. No. 60/124,417, filed Mar. 15, 1999.

The present invention relates to method for producing polyhydroxyalkanoates in recombinant organisms.

BACKGROUND OF THE INVENTION

Plastic materials have become an integral part of contemporary life because they possess many desirable properties, including durability and resistance to degradation. Over the past 10–20 years, their widespread use have been increasingly regarded as a source of environmental and waste management problems. Industrial societies are now more aware of the impact of discarded plastic on the environment, and of their deleterious effect on wildlife and the aesthetic qualities of cities and forests. Problems associated with the disposal of waste and reduction in the availability of landfills have also focused attention on plastics, which accumulate in the environment at a rate of 25 million tonnes per year (Lee, 1996). These problems have created much interest in the development and production of biodegradable plastics. Biodegradable polymers are composed of material which can be degraded either by non-enzymatic hydrolysis or by the action of enzymes secreted by microorganisms. Estimates of the current global market for these biodegradable plastics range up to 1.3 billion kg per year (Lindsay, 1992).

Among the various biodegradable plastics available, there is a growing interest in the group of polyhydroxyalkanoates (PHAs). These are natural polymers produced by a variety of bacteria and they are 100% biodegradable. By changing the carbon source and bacterial strains used in the fermentation processes, PHA-biopolymers having a wide variety of mechanical properties have been produced. Their physical characteristics range from hard crystalline to elastic, depending on the composition of monomer units (Anderson & Dawes, 1990). The majority of PHAs are composed of R-(−)-3-hydroxyalkanoic acid monomers ranging from 3 to 14 carbons in length (C3–C14). The simplest member of the family, P(3HB) (C4), is highly crystalline, relatively stiff, and becomes brittle over a period of days upon storage under ambient conditions (Barham et al., 1984; De Koning et al., 1992; Doi, 1990; Holmes, 1988). Therefore, attempts have been made to decrease the brittleness of P(3HB) either by incorporating comonomers such as P(3HV), by blending with other polymers or blending with chemically synthesized atactic P(3HB) (Holmes, 1988; Kumagai & Doi, 1992 a, 1992 b, 1992 c; Pearce & Marchessault, 1994).

The P(3HB-co-3HV) copolymer, developed by ZENECA under the tradename BIOPOL™, has improved mechanical properties compared to P(3HB). As the fraction of P(3HV) (C5) increases, the polymer becomes tougher, more flexible and have an higher elongation to break (Doi et al., 1990). The medium-chain-length (MCL) PHAs are semicrystalline elastomers with a low melting point, low tensile strength, and high elongation to break. They thus have physico-chemical characteristics that make them more appealing than homogeneous P(3HB); they can even be used as a biodegradable rubber after cross linking by electron-beam irradiation (De Koning et al., 1994; Gagnon et al., 1992; Gross et al., 1989; Preusting et al., 1990).

PHAs have been shown to occur in over 90 genera of Gram-positive and Gram-negative bacteria species (Steinbüchel, 1991). Over 40 different PHAs have been characterized, with some polymers containing unsaturated bonds or various functional groups (Steinbüchel, 1991). Bacteria synthetise and accumulate PHAs as carbon and energy storage materials or as a sink for redundant reducing power under the condition of limiting nutrients in the presence of excess carbon sources (Byrom, 1994; Doi, 1990; Steinbüchel & Valentin, 1995). When the supply of the limiting nutrient is restored, the PHAs are degraded by intracellular depolymerases and subsequently metabolized as carbon and energy source (Byrom, 1990; Doi, 1990). The monomer 3HAs released from degradation of these microbial polyesters are all in the R-(−)-configuration due to the stereo specificity of biosynthetic enzymes (Anderson & Dawes, 1990). The molecular weights of polymers are in the range of $2 \times 10^5$ to $3 \times 10^6$ Daltons, depending on the microorganism and growth condition (Byrom, 1994). PHAs accumulate in the cells as discrete granules, the number per cell and size of which can vary among the different species; 8 to 13 granules per cell of 0.2 to 0.5 $\mu$m diameter have been observed in *Alcaligenes eutrophus* (Byrom, 1994).

PHAs can be subdivided in two groups depending on the number of carbon atoms in the monomer units: short-chain-length-(SCL) PHAs, which contain 3–5 carbon atoms, and medium-chain-length-(MCL) PHAs, which contain 6–14 carbon atoms (Anderson & Dawes, 1990). This is mainly due to the substrate specificity of the PHA synthases that can only accept 3HA monomers of a certain range of carbon lengths (Anderson & Dawes, 1990). The PHA synthase of *Alcaligenes eutrophus* can polymerize C3–C5 monomers, but not C6 or higher. On the other hand, the PHA synthase of *Pseudomonas oleovorans* only accepts C6–C14 monomers. Of particular interest is the capacity of some PHA synthase to polymerize 3-hydroxy-, 4-hydroxy- and 5-hydroxy-alkanoates (Steinbüchel & Schlegel, 1991). Even though most of the PHA synthases examined to date are specific for the synthesis of either SCL- or MCL-PHAs, at least six cases were recently reported in which the bacteria were able to synthesize copolymer consisting of SCL and MCL units (Lee, 1996).

P(3HB) is the most widespread and thoroughly characterized PHA, and most of the knowledge has been obtained from *Alcaligenes eutrophus* (Steinbüchel, 1991). In this bacterium, P(3HB) is synthesized from acetyl-CoA by the sequential action of three enzymes (FIG. 1). The first one, 3-ketothiolase, catalyses the reversible condensation of two acetyl-CoA moieties to form acetoacetyl-CoA. Acetoacetyl-CoA reductase subsequently reduces acetoacetyl-CoA to R-(−)-3-hydroxybutyryl-CoA, which is then polymerized by the action of PHA synthase to form P(3HB). A number of PHAs with different C3 to C5 monomers have been produced in *A. eutrophus*, the nature and proportion of these monomers being influenced by the type and relative quantity of the carbon sources supplied to the growth media (Steinbüchel & Valentin, 1995). *Pseudomonas oleovorans* and most pseudomonades belonging to the ribosomal rRNA homology group I synthesize MCL-PHAs from various MCL-alkanes, alkanols, or alkanoates (Steinbüchel & Valentin, 1995). The composition of PHA produced is related to the substrate used for growth, with the polymer being mostly composed of monomers which are 2n carbons shorter than the substrates used. It was suggested that the acyl-CoA derived from alkanoic acids enter the β-oxidation pathway and R-(−)-3hydroxyacyl-CoA intermediates used by the PHA synthase are generated either through reduction of 3-ketoacyl-CoA by a ketoacyl-CoA reductase, conversion of S-(+)-3hydroxyacyl-CoA normally produced by the pathway to the R-(-)-isomer by an epimerase, or the direct hydration of enoyl-CoA by an enoyl-CoA hydratase (Poirier et al., 1995).

Most pseudomonades belonging to rRNA homology group I, except *P. oleovorans*, also synthesize MCL-PHAs when grown on substrates non related to fatty acids and alkanoates, such as gluconate, lactate, glycerol, and hexoses (Anderson & Dawes, 1990; Huijberts et al., 1994; Timm & Steinbüchel, 1990). These substrates must be first converted into acetyl-CoA to be used for the PHAs biosynthesis. This suggests that, in theory, microorganisms, plants and even animals, must be able to synthesize PHA following the transfection of a limited number of genes. In these bacteria, three main pathways have been proposed for the synthesis of PHA precursors (Huijberts et al., 1992, 1994).

(i) A detailed analysis of the composition of PHA produced by *P. putida* grown on glucose have shown that the monomers are structurally identical to the acyl-moieties of the 3-hydroxyacyl-ACP intermediates of the novo fatty acid biosynthesis. Since it has not been shown that PHA synthase can accept acyl-ACPs as substrates, these must therefore be converted to acyl-CoAs by a transacylase before entering the PHA pathway.

(ii) Fatty acid degradation by β-oxidation is the main pathway when fatty acids are used as substrate.

(iii) It has been found that some of the monomeric units of PHA are one C2 unit longer than the fatty acid used as substrate. Chain elongation by condensation of an acetyl-CoA to the acyl-CoA has therefore been suggested.

A complex picture thus emerges in which the steps linking the different pathways implied and PHA synthesis are at present unknown (FIG. 2). It is assumed, but not demonstrated, that the ultimate substrate for polymerization is the R form of the CoA-activated 3-hydroxy fatty acid intermediates. Expression of the synthases of *P. putida* in wild-type *E. coli* is not sufficient to produce PHA in this bacterium (Huisman, 1991). More genetic information from Pseudomonas spp. seems to be needed to enable PHA synthesis in *Escherichia coli*. We can speculate that the missing step in prokaryotic organisms other than pseudomonades is the formation of R-(-)-3-OH-acyl-CoA of more than 5C.

The bio(techno)logical approach for the production of PHAs use microbial systems. The major commercial drawback of the so-produced bacterial PHAs are their high production cost, making them substantially more expensive than synthetic plastics. At present, Zeneca produces approximately 1,000 tons per year of P(3HB-co-3HV) copolymer at a cost of approximately $16/kg. At a production rate of 10,000 tons per year or more, the most optimistic scenario would put the cost at $5/kg. With the cost of many synthetic plastics such as polypropylene and polyethylene, being less than $1/kg, PHA appear too costly for most low-value consumer products (Poirier et al., 1995).

Engineering of novel pathways in eucaryotic cell systems seems to be a beneficial alternative to the production of PHAs in bacteria. On one hand, yeast and insect cells can be used as models to gain information on PHAs synthesis in eucaryotes (Hahn et al., 1996; Sherman, 1996). On the other hand, a new possibility for the production of PHAs on a large scale and at costs comparable to synthetic plastics has arisen from the demonstration of their production in transgenic plants (Poirier et al., 1992). Production of PHA on an agronomic scale could allow synthesis of biodegradable plastics in the million ton scale compared to fermentation which produces material in the thousand ton scale (Poirier et al., 1995). In addition, plant production of PHAs would use carbon dioxide, water and sunlight as raw materials to produce PHA in an environmentally friendly and sustainable manner.

Synthesis of PHB in plants was initially explored by expression of the PHB biosynthetic genes of *A. eutrophus* in the plant *Arabidopsis thaliana* (Poirier et al., 1992). Although of no agricultural importance, this small oil seed plant was chosen for its extensive use as a model system for genetic and molecular studies in plants. These plants accumulated P(3HB) granules that were 0.2 to 0.5 $\mu$m in diameter in the nucleus, vacuole, and cytoplasm. However, the amount of P(3HB) accumulated was only 100 $\mu$g/g fresh weight. Furthermore, plants were impaired in their growth, probably due to the severe deviation of substrate from the mevalonate pathway which is essential for chlorophyll synthesis.

To avoid this problem and to improve polymer accumulation, further genetic manipulation have been carried out to divert reduced carbon away from endogenous metabolic pathways and to regulate the tissue specificity and timing of gene expression. The plastid was suggested to be the ideal location for P(3HB) accumulation because it is the location of high flux of carbon through acetyl-CoA. Genetically engineered genes of *A. eutrophus* were then successfully targeted to the plant plastids, where the enzymes were active (Nawrath et al., 1995). The *A. eutrophus* PHA biosynthesis genes were modified for plastid targeting by fusing the transit peptide of ribulose biphosphate carboxylase to their N-terminal ends and were put under the control of the constitutive CaMV 35S promoter. The hybrid expressing the *A. eutrophus* PHA synthesis enzymes accumulated P(3HB) up to 10 mg/g fresh weight, representing ca. 14% of dry weight.

The knowledge acquired in this study is not only useful to optimise strategies for the production of PHB in recombinant organisms, but could also be used for the production of PHAs other than PHB, for example MCL-PHAs. For plant production of PHAs to become commercially viable, the genes must be transfected into a suitable plant species which has the agronomic properties to provide high yields of PHA per hectare, at unlimited scale and at economic prices. Subcellular localization signals and promoters must be chosen which allow the enzymes utilized to intercept the desired plant metabolites for incorporation into the polymer.

Different strategies have been proposed for production of PHAs in plants. Substitution of cytoplasmic oil bodies by PHA granules, production of PHAs in glyoxysomes or production of PHAs in leucoplasts have been proposed to be carried out in lipid-accumulating tissues of oilseed crops, such as seed endosperm or fruit mesocarp (van der Leij & Witholt, 1995; Hahn et al., 1996; Srienc & Leaf, 1996). In this tissue, triglycerides provide energy and carbon for germination of the new plant before establishment of photosynthesis. In contrast, PHAs would not be degraded in plants because of the absence of endogenous enzymes capable of hydrolyzing the polymer. Interfering with synthesis and degradation of fatty acids, in respectively plastids and glyoxysomes, by diverting energy into PHAs in this stage of development is likely to impair germination and/or seedling growth. As a post-harvest event this can be desirable. However, this inherent characteristic of the proposed strategy will create problems in the production of viable hybrid seeds. The expression of the enzymes during germination should be restricted to the second generation of seeds or fruit. For this, solutions will have to be found. It is probable that controlled expression of these genes will necessitate the use of promoters stimulated by external signals (Williams et al., 1992).

Plastids are regarded as the most amenable targets for PHA production. The production in chloroplasts, directly coupled to the novo fatty acid synthesis has many advantages. First, every important crop can be used. Second, in leaves, fatty acid metabolism is not as important as in seeds and targeting to this tissue is not likely to impair growth of the plant. Third, it is the most direct way for PHAs production, since the plant does not have to produce long-chain fatty acids or triglycerol before diverting fatty acid degradation products into PHAs, like in the case of glyoxysomal degradative mechanisms. Fourth, as shown for the synthesis of PHB, compartmentalization in plastids does not impair growth and then appear to be favoured over unrestricted synthesis in the cytosol.

*Pseudomonas aeruginosa* belongs to the group of pseudomonades of the rRNA homology group I that synthesize MCL-PHAs when grown either on alkanes or on unrelated substrates such as gluconate (Timm & Steinbüchel, 1990). A PHA synthase locus in *P. aeruginosa* was identified by the use of a $^{32}$P-labeled 30-mer synthetic oligonucleotide probe, whose sequence design was based on that of a highly conserved region of PHA synthases in *A. eutrophus* and *P. oleovorans* (Steinbüchel et al., 1992). The organization of the locus consist of two genes coding for PHA synthases (phaC1, phaC2) separated by a gene coding for a putative PHA depolymerase (phaD), and a fourth gene (ORF3) downstream of phaC2 with an unknown function (Timm & Steinbüchel, 1992). It has been shown that these synthases are similar to those found in *P. oleovorans*, who is unable to synthesize MCL-PHAs from unrelated substrates (Huijberts et al., 1992).

As was shown in *P. aeruginosa*, intermediates of fatty acid biosynthesis and β-oxidation are likely to contribute to the formation of PHA polymers. It is most likely that the intermediate precursors to PHA synthesis are either ketoacyl-CoA, S-(+)-3-OH-acyl-CoA, enoyl-CoA, or R-(−)-3-OH-acyl-ACP. However, since substrate specificity for PHA synthase has not yet been thoroughly tested, it is still unclear whether this enzyme could accept other derivative forms of 3-hydroxyacyl moieties, like for instance ACP derivatives. This can be of substantial impact on the choice of the best strategy for production in recombinant organisms: if the recombinant enzyme can accept, even at suboptimum rates, ACP derivatives as substrate, then its targeting to chloroplasts would be the only required engineering alteration needed to induce PHA accumulation in leaf cells.

Monomeric units of PHAs, as it is the case for these of PHBs, are of the isomeric form R-(−)-; this has been repeatedly demonstrated by the analysis of hydrolysate from PHA granules. Enzymologic analysis also show that PHB synthases have a definite specificity for R-(−)-3-OH-acyl-CoA as substrates. Although the substrate specificity of PHA synthases has not yet been thoroughly characterized with purified enzyme preparations, their high homology with PHB syntheses and the analysis of their reaction product strongly suggest that they share a preference for R-(−)-3-OH-acyl CoA substrates with PHB synthases.

There are no demonstration of a metabolic pathway that would supply monomeric subunits to the polymerization reaction in Pseudomonades, nor in any other organisms. Known degradation pathways starting with acyl-CoAs produce S-(−)3-OH-acyl-CoAs and synthetic pathways produce R-(−)-acyl-ACPs, none of which can serve as substrate for the PHA synthesis reaction.

As further background, the following U.S. Patent should be reviewed: 5,650,555; 5,502,273; 5,245,023; 5,610,041; 5,229,279; 5,534,432; 5,750,848; 5,663,063; 5,480,794; 5,750,848; 5,801,027; 5,298,421 and 5,250,430.

SUMMARY OF THE INVENTION

This invention is directed at the production of polyhydroxyalkanoates in recombinant organisms, through the engineering of a new metabolic pathway which produces R-(−)-3-OH-acyl-CoAs monomeric subunits of adequate length to serve as substrates for the activity of PHA synthases.

More specifically, it describes the methodology that is used to produce transgenic organism with a new metabolic pathway that partially deviates fatty acids from their normal synthetic pathways, towards the formation of R-(−)-3-OH-acyl-CoAs that serves as substrates for the synthesis of hydroxyalkanoate polymers in chloroplasts.

The engineered synthetic metabolic pathway of the present invention initially produces free ($C_8$) fatty acids from the fatty acid synthesis pathway through the action of a thioesterase, that will then add a CoA moiety to the free fatty acid through the action of an acyl-CoA synthase, that will produce 3-(−)-ketoacyl-CoAs from the acyl-CoA through the action of athiolase, that will produce R-(−)-OH-acyl-CoAs from the 3-keto acid-CoAs through the action of a unique dehydrogenase isoform from yeast. These R-(−)-3-OH-acyl-CoAs will finally be used as substrate for the PHA synthase reaction.

Thus according to the present invention there is provided a method for the production of polyhydroxyalkanoates comprising: selecting a transgenic organism comprising a foreign DNA sequence encoding an enzyme having dehydrogenase activity, which will produce a R-(−)-hydroxyacyl-CoA from a keto acid-CoA, wherein said R-(−)-hydroxyacyl-CoA will serve as a substrate for polyhydroxyalkanoate synthase; and producing said polyhydroxyalkanoate.

Further, according to the present invention there is provided a method for producing a polyhydroxyalkanoate in a host comprising: selecting a host for expression of genes encoding enzymes required for synthesis of a polyhydroxyalkanoate; introducing into said host structural genes encoding enzymes selected from the group consisting of: a thioesterase, an acyl-CoA synthetase, a thiolase, a hydroxyacyl-CoA dehydrogenase, and a polyhydroxyalkanoate synthase; expressing the enzymes encoded by the genes; and providing the appropriate substrates for the expressed enzymes to synthesis the polyhydroxyalkanoate.

According to the present invention there is also provided a cloning vector comprising foreign DNA encoding an enzyme having dehydrogenase activity, which will produce R-(−)-hydroxyacyl-CoA from a keto acid-CoA. According to one embodiment of the invention the cloning vector further comprises a DNA sequence encoding an enzyme having thioesterase activity; an enzyme having acyl-CoA synthetase activity; an enzyme having thiolase activity; and an enzyme having polyhydroxyalkanoate synthase activity.

According to the present invention there is also provided a host cell comprising foreign DNA encoding an enzyme having dehydrogenase activity, which will produce R-(−)-hydroxyacyl-CoA from a keto acid-CoA. According to one embodiment of the invention the host cell further comprises a DNA sequence encoding an enzyme having thioesterase activity; an enzyme having acyl-CoA synthetase activity; an enzyme having thiolase activity; and an enzyme having polyhydroxyalkanoate synthase activity.

According to the present invention there is also provided a transgenic organism comprising foreign DNA encoding an enzyme having dehydrogenase activity, which will produce R-(−)-hydroxyacyl-CoA from a keto acid-CoA. According to one embodiment of the invention the transgenic organism further comprises a DNA sequence encoding an enzyme having thioesterase activity; an enzyme having acyl-CoA synthetase activity; an enzyme having thiolase activity; and an enzyme having polyhydroxyalkanoate synthase activity. In one example of this embodiment the transgenic organism is a plant.

BRIEF DESCRIPTION OF THE DRAWINGS

These and other features of the invention will become more apparent from the following description in which reference is made to the appended drawings wherein:

FIG. 4 shows the DNA constructs of the present invention.

FIGS. 5A–5J show the DNA sequences for pKitmus/Rbsck-DH-3' nc, FIGS. 5A–5C (SEQ ID NO: 1) (The sites SalI, SphI, ApaI, EcoRI and SmaI are underlined and the ATG site is in bold); pUC/35S.C4PPDK.DH.3' nc, FIGS. 5D–5E (SEQ ID NO: 2) (XhoI, SphI, ApaI and EcoRI sites are underlined and the ATG of the protein is in bold); and pCambia/RbscK-DH-3' nc, FIGS. 5F–5J (SEQ ID NO: 3) (SalI, SphI, ApaI, EcoRI and SmaI sites are underlined and the ATG of the protein is in bold.

DESCRIPTION OF PREFERRED EMBODIMENT

The present invention is directed at the production of polyhydroxyalkanoates in recombinant organisms, through the engineering of a new metabolic pathway which produces R-(−)-3-OH-acyl-CoAs monomeric subunits of adequate length to serve as substrates for the activity of PHA synthases.

Figure 1:
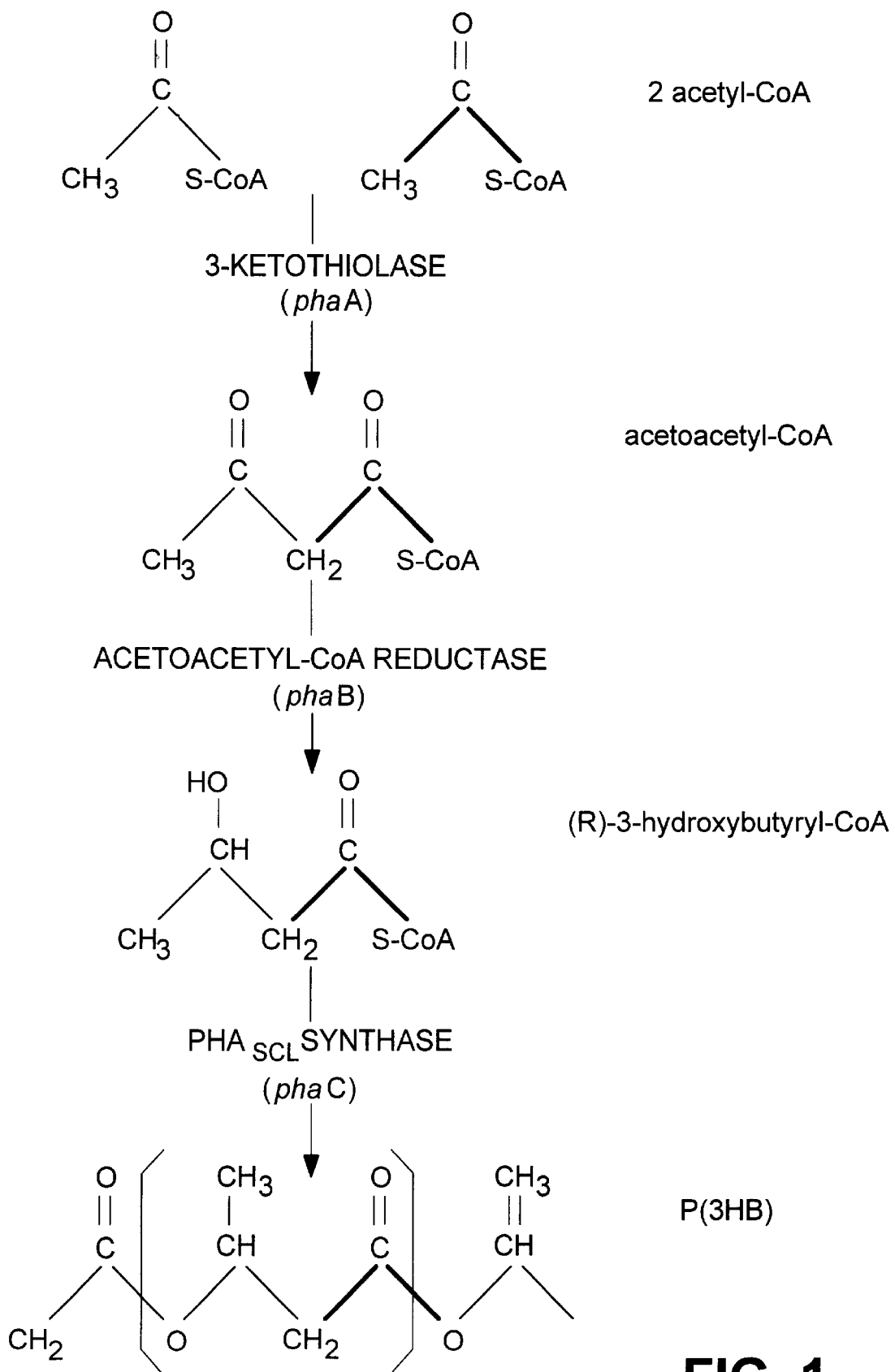
FIG. 1 shows the pathway for the production of P(3HB) by *Alcaligenes eutrophus*.
Figure 2:
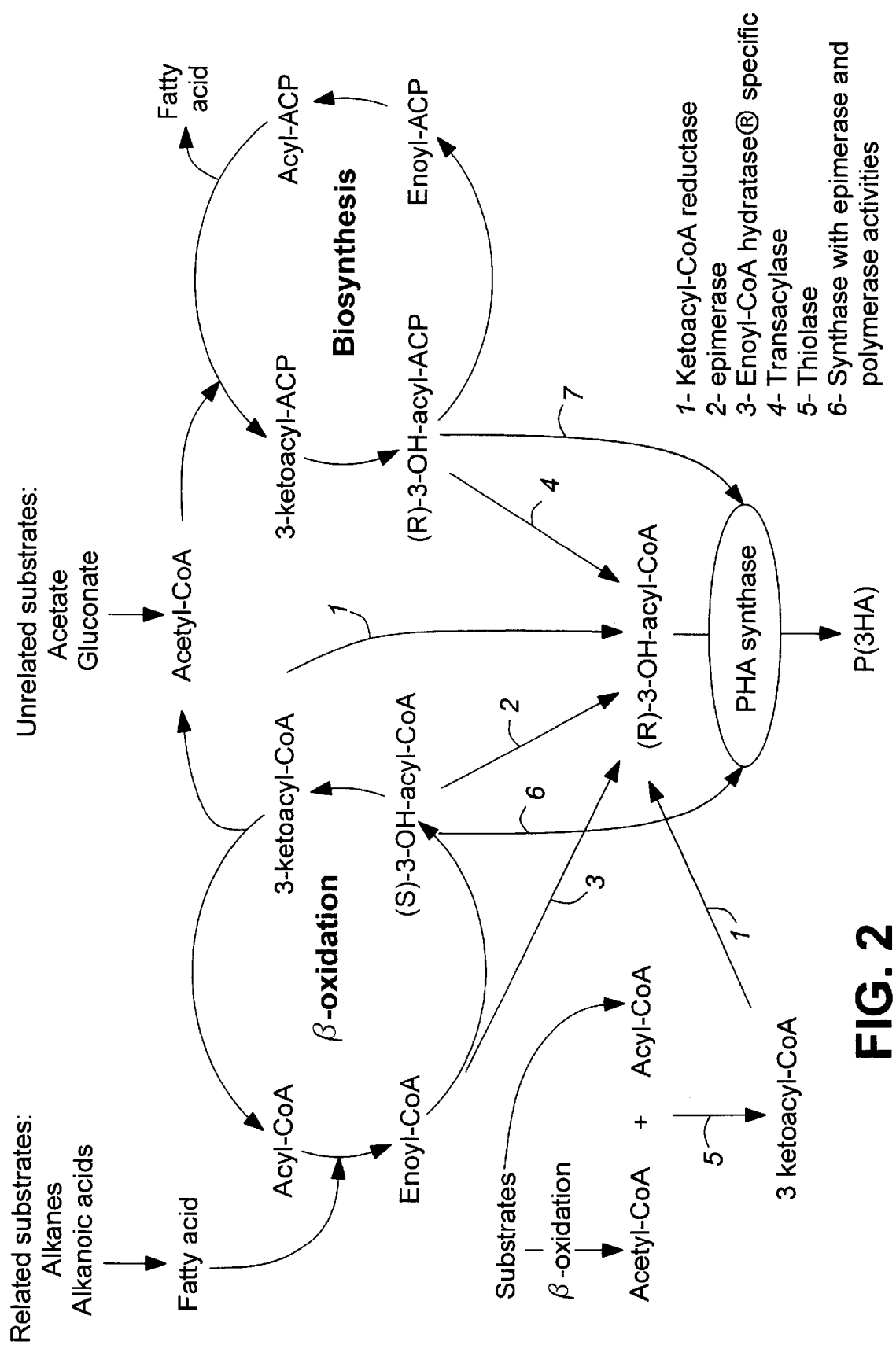
FIG. 2 is a hypothetical pathway for the synthesis of PHAs from Pseudomonades.
Figure 3:
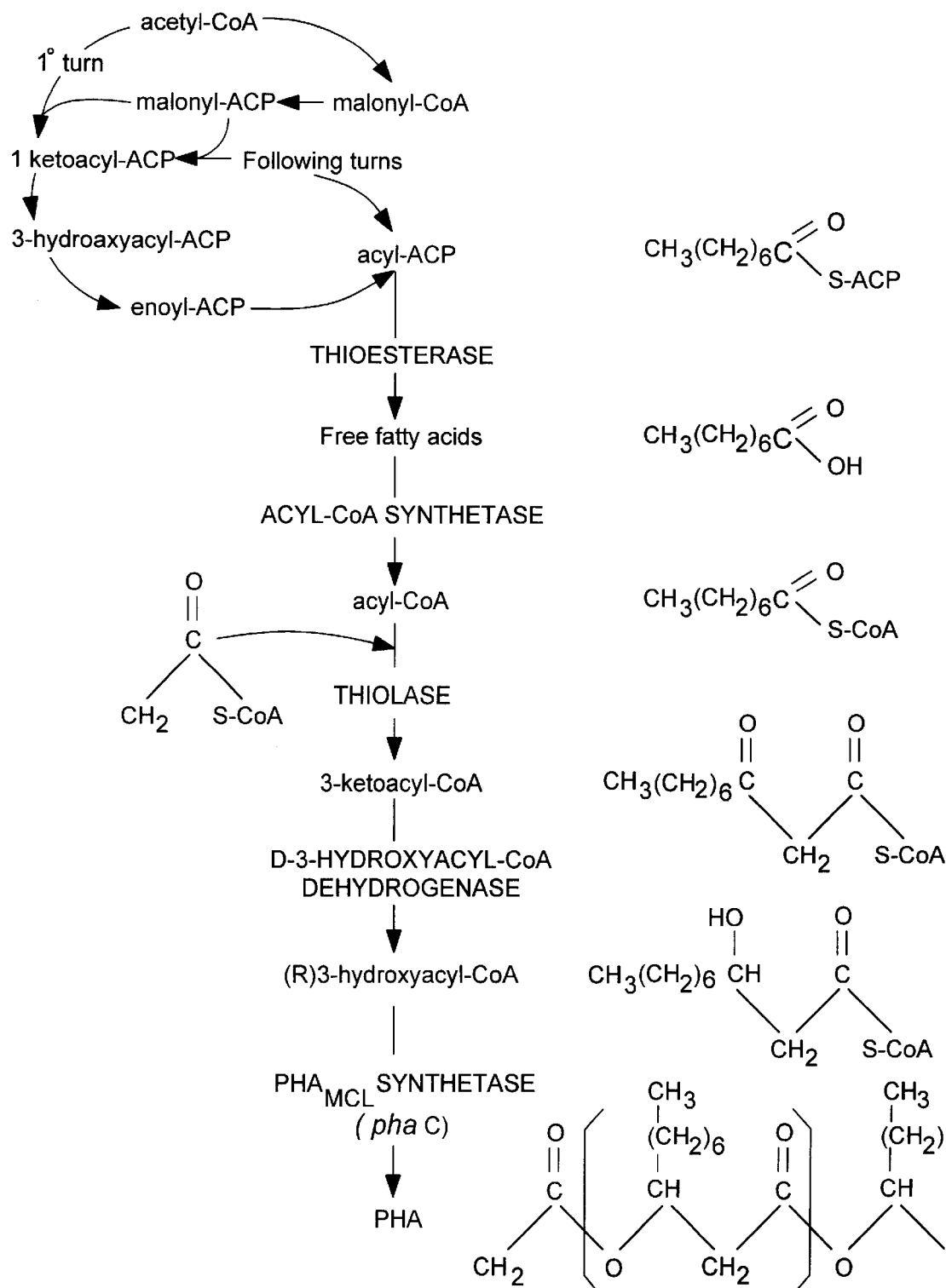
FIG. 3 is the synthetic pathway of the present invention showing the five steps involved in the production of medium chain length PHAs.

More specifically, the present invention is directed to a methodology that is used to produce transgenic organisms with a new metabolic pathway that partially deviates fatty acids from their normal synthetic pathways, towards the formation of R-(−)-3-OH-acyl-CoAs that serves as substrates for the synthesis of hydroxyalkanoate polymers in chloroplasts. The new synthetic pathway of the present invention is depicted in FIG. 3.

In one embodiment of the present invention the transgenic organism is a plant or any organ of a plant where there is active plastid activity.

According to the present invention examples of suitable plants include but are not limited to Arabidopsis, tobacco, alfalfa and tuber plants such as potato, sweet potato, beet and cassava.

Prior to the present invention, there was no demonstration of a metabolic pathway that would supply monomeric subunits to the polymerization reaction in Pseudomonades, nor in any other organisms. Known degradation pathways starting with acyl-CoAs produce S-(−)3-OH-acyl-CoAs and synthetic pathways produce R-(−)-acyl-ACPs, none of which can serve as substrate for the PHA synthesis reaction. Thus, the present invention is directed to a synthetic pathway that will produce R-(−)-OH-acyl-CoAs from 3-keto acid-CoAs through the action of a dehydrogenase isoform from yeast. These R-(−)-OH-acyl-CoAs will then serve as a substrate for the PHA synthase reaction.

According to the present invention the term polyhydroxyalkanoate, is intended to include a polymer of R-(−)-3-hydoxyalkanoic acid monomers from about 3 to about 14 carbons in length. In one embodiment of the present invention the PHA synthase from *Pseudamonas aeruginosa* is used in the last step of the synthetic pathway. This enzyme prefers R-(−)-3-OH-acyl-CoAs of C6 to C 14 as a substrate.

The biosynthetic pathway of the present invention involves five enzymes: a thioesterase, a acyl-CoA synthetase, a thiolase, a D-3-hydoxyacyl-CoA dehydrogenase and a PHA synthase.

The first reaction is catalyzed by a thioesterase. In one embodiment of the present invention the enzyme has been cloned from a cDNA library from *Cuphea hookeriana*, a Mexican bush plant which accumulates up to 75% of C8:0- and C10:0-fatty acids in seeds. This clone Cl FatB2 (GenBank accession # U39834) has been expressed in *E. coli* where it exhibited a high specificity for C8:0 and C10:0-ACPs as substrates. In the chloroplasts, this enzyme removes C8- and C10-acyl-ACPs from the fatty acid synthetic pathway and releases free medium-chain length fatty acids in the stroma much as endogenous thioesterases do with C 16- and C18-acyls-ACPs in the fatty acid synthetic pathway (Dehesh, K. et al., 1996, The Plant Journal 9(2): 167–172).

The second reaction is catalysed by an acyl-CoA synthetase. In one embodiment of the invention, the enzyme was isolated from *Pseudomonas oleovorans*, a bacteria which accumulates $PHAs_{mcl}$ (medium-chain length polyhydroxy alkanoates). The enzyme is encoded by gene K of operon alkBFGHJKL which is responsible for alkanoate synthesis. This acyl-CoA synthetase (GenBank accession # X65936) is specific to medium-chain length fatty acids (van Beilen, J. B. et al. (1992) DNA sequence determination and functional characterization of the OCT-plasmid-encoded alkJKL genes of *Pseudomonas oleovorans*. Molecular Microbiology 6(21): 3121–3136).

The third reaction is catalysed by a keto thiolase. This reaction is a condensation reaction which will add one acetyl-CoA moiety to the acyl-CoA, thus releasing one CoA molecule. This condensation reaction is reversible, and creates a 3-keto acyl CoA with two extra carbon. The products following this reaction will be therefore C10- and C12-3-OH-acyl CoAs and free CoA. The enzyme described in one example of the present invention has been isolated from Brassica napus, in which it is part of the oxidation pathway (Olesen, C. J. et al. (1997) The glyoxysomal 3-ketoacyl-CoA thiolase precursor from *Brassica napus* has enzymatic activity when synthesized in *E. coli* (FEBS Letters 6(21): 138–140; GenBank accession # X93015).

The fourth reaction, according to the present invention, is catalysed by a yeast 3-hydroxyacyl-CoA dehydrogenase which produces R-(−)-3-OH-acyl-CoAs (Hiltunen, J. K. et al. (1992) Peroxisomal multi functional β-oxidation protein of *Saccharomyces cerevisiae*. J. Biol. Chem. 267:6646–6653; GenBank accession # M86456). Homologs of this 3-keto-acyl-CoA dehydrogenases usually produce S-(−)-3-OH-acyl-CoAs in the β-oxidation pathway. The 3-hydroxyacyl-CoA dehydrogenase domain of the multi functional protein (MFP) of yeasts exhibits this unique catalytic property. Thus the product of this reaction will be R-(−)-3-OH-decanoyl-CoA and R-(−)-3-OH-dodecanoyl-CoA. Both molecules can serve as substrate for the polymerization reaction catalyzed by PHA synthases.

The last reaction of this embodiment is catalysed by a PHA synthase from *Pseudomonas aeruginosa*, which accumulates large amounts of PHA granules in nutrient stress conditions (Timm, A. and Steinbüchel, A., 1992) Cloning and molecular analysis of the poly(3-hydroxyalkanoic acid) gene locus of *Pseudomonas aeruginosa* PAO1. Eur. J. Appl. Microbiol. 209: 15–30; GenBank accession # X66592). Analysis of depolymerization products shows that this enzyme uses R-(−)-3-OH-acyl-CoAs of C6 to C14 in length as substrates, with an apparent preference for C10 and C12 R-(−)-3-OH-acyl-CoAs.

In one embodiment of the present invention, each of these genes is sub-cloned in an appropriate expression vector. In one embodiment of this invention the host is a plant cell and any know plant expression vector can be used according to the present invention. Said plant expression vector can contain a promoter sequence, a 5'UTR sequence, a chloroplast transit peptide sequence, the complete coding sequence of the gene, a stop codon, an a 3'UTR region containing a eukaryotic polyadenylation signal and a polyadenylation site. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

This invention is directed at any means by which the genes of interest can be transfected in a plant providing it results in stable integration and expression. Preferred means are, Agrobacterium mediated DNA transfer which requires T-DNA borders, and selectable markers; DNA bombardment, which requires selectable markers, and electroporation which can in some cases be used without screenable markers. These various cloning and plant transformation methods are well know in the art. For reviews of such techniques see for example Weissbach and Weissbach, *Methods for Plant Molecular Biology*, Academy Press, New York VIII, pp. 421–463 (1988); and Geierson and Corey, Plant *Molecular Biology,* 2d Ed. (1988).

Also considered part of this invention are transgenic organisms containing the chimeric gene construct of the present invention. In one embodiment of this invention the transgenic organism is a plant. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

When specific sequences are referred to in the present invention, it is understood that these sequences include within their scope sequences that are "substantially similar" to said specific sequences. Sequences are "substantially similar" when at least about 80%, preferably at least about 90% and most preferably at least about 95% of the nucleotides match over a defined length of the molecule. Sequences that are "substantially similar" include any substitution, deletion, or addition within the sequence. DNA sequences that are substantially similar can be identified in Southern hybridization experiments, for example under stringent hybridization conditions (see Maniatis et al., in Molecular Cloning (A Laboratory Manual), Cold Spring Harbor Laboratory (1982) p 387 to 389).

The specific sequences, referred to in the present invention, also include sequences which are "functionally equivalent" to said specific sequences. In the present invention functionally equivalent sequences refer to sequences which although not identical to the specific sequences provide the same or substantially the same function. DNA sequences that are functionally equivalent include any substitution, deletion or addition within the sequence.

Since the creation of the novel metabolic pathway requires the simultaneous expression of 5 different transgenes, 5 independent transformants can be produced, and genotypes containing the 5 transgenes are produced by repeated crossing of mono-transgenics and selection. Alternately, series of genes can be co-transfected on single constructs, thus reducing the need for extensive crossing. Other means of integrating the novel genes in chloroplasts also include the direct transfection of DNA on chloroplastic DNA by recombination using homologous or heterologous border sequences. Using this methodology, polycistronic constructs (multiple gene construct under the control of a single promoter) could be used to bring the 5 modifications. These methods are well known to persons of skill in the art.

While this invention is described in detail with particular reference to preferred embodiments thereof, said embodiments are offered to illustrate but not limit the invention, as shown in the following example.

EXAMPLES

PHA synthase

Cloning of the PHA synthase gene PhaC1 (X66592, Timm, 1992) was performed by PCR amplification of genomic DNA from *Pseudomonas aeruginosa* strain PAO1 with the "Expand" system from Boehringer Mannheim. Template DNA was extracted and purified. The primer at the 5' terminus was 5'GATC GCATGC GAAGGATTTC T ATGAGTCAG3' (SEQ ID NO:4); it contains the SphI and XmnI restriction sites upstream from the ATG. The primer at the 3'terminus was 5'GATC GAATTCTCATCGTTCATGCACGTAGG3' (SEQ ID NO:5); a EcoRI site had been introduced downstream of the stop codon. Conditions for the PCR were: 94° C.-2'

| denaturation: | 94° C.–10" | 10 cycles |
|---|---|---|
| annealing: | 55° C.–30" | |
| polymerization: | 68° C.–4' | |
| denaturation: | 94° C.–10" | 20 cycles |
| annealing: | 55° C.–30" | |
| polymerization: | 68° C.–4' d 20"/cycle | |

68° C.-7'

The PCR products formed were separated on agarose gels and the band corresponding to the expected size was removed from the gel. Purified DNA was then digested with SphI/EcoRI, and the 1692 pb fragments were cloned in pUC1 8. Complete homology of the selected clone was verified by sequencing. The synthase gene was then cloned at the SphI/EcoRI sites of pGEM-7Zf (Promega) containing the 3'non coding region (3'nc) of SSU-rubisco gene RbcsK (Khoudi et al 1997) previously cloned at the EcoRI/SmaI site. The SphI/SacI fragment (2138 pb) containing PhaC1+ 3'nc was then sub-cloned into Litmus28 (NE Biolabs) containing the complete 5' region of RbcsK with the promoter and transit peptide (5' RbcsK), previously cloned at the SalI/SphI site. Finally, a fragment of 4112 bp containing the 5'RbcsK+PhaC1+3'nc was cloned into the SalI/SacI site of pBI 101.2 (Clontech), removing then the GUS gene. This construct was then transfected to *Agrobacterium tumefaciens* strain LBA4404, and incorporated in the genome of selected plant cells cells through co-cultivation with transgenic *A. tumefaciens*, as described by Desgagnés et al (1995) Plants were regenerated from transgenic cells, and leaf tissue is used for the selection of the best transgenic lines by Northern analysis. PHA synthase activity of the selected lines was then measured in clarified leaf extracts as described in the prior art.

Hydroxyacyl-CoA Dehydrogenase

The domain of the multi functional b-oxidation protein (MFP) (M86456) (Hiltunen, 1992) which encodes for R-3-hydroxyacyl-CoA dehydrogenase was amplified by PCR from *Saccharomyces cerevisiae*. It has been shown that the protein contains two activities: a 2-enoyl-CoA hydratase 2, converting trans-2-enoyl-CoA to R-3-hydroxyacyl-CoA, and a R-3-hydroxyacyl-CoA dehydrogenase, converting R-3-hydroxyacyl-CoA to 3-ketoacyl-CoA. A truncated version of MFP lacking 271 carboxyl-terminal amino acids was also overexpressed and purified and it was shown that it has only the R-3-hydroxyacyl-CoA dehydrogenase activity. These results clearly demonstrate that the b-oxidation of fatty acids in the yeast follows a previously unknown stereochemical course, namely it occurs via a R-3-hydroxyacyl- CoA intermediates.

The expression of the truncated version in chloroplasts of plants with a medium-chain length- specific thioesterase, an acyl-CoA synthetase and a thiolase will allow the production of R-3-hydrozyacyl-CoAs, the substrate of the PHA synthase.

Template genomic DNA was extracted and purified from *S. cerevisiae* as described in Current Protocols in Molecular Biology, 1997, section 13.11.1–13.11.4. The 5' primer used contains the SphI site upstream of the ATG (GATC GCATGCTAATGCCTGGAAATTTATCCTTC) (SEQ ID NO:6) and the 3' primer has an ApaI site downstream a newly introduced stop codon (GATC GGGCCCTTACGGGTTGATAGTGTTGCGACT) (SEQ ID NO:7). The PCR conditions are described above, except that the annealing temperature used was 50° C. The PCR fragment was purified, digested SphI/ApaI and the 1799 bp fragment was cloned in pKitmus/RbscK-3'nc. This vector is a pLitmus28 derivative that contains a cassette for chloroplasts expression. This cassette has in 5' the promoter of the small subunit of the ribulose 1,5-biphosphate carboxylase (rubisco) of alfalfa, its 5' non-translated region and the targeting signal to chloroplasts, followed by a multiple cloning site (MCS), and in 3', the 3' non coding region of rubisco (Khoudi, et al., 1997). The region in 5' is a 1978 bp SalI/SphI fragment that has at its 3' end the sequence that codes for the 58 amino acids of the transit peptide, followed by the ATG of the mature protein. This ATG is found to be the one in the SphI site. The dehydrogenase clone in the MCS is then in frame with the targeting signal, having a leucine in between the ATG of the mature rubisco protein and the one of the gene.

The 3' non coding region is a 441 bp EcoRI/SmaI fragment that has the two PolyA signals of the small subunit of rubisco.

A potential clone has been sequenced with these primers:

Jonc. Rub. 5' AAGTCCATGGCTGGCTTCCCA (SEQ ID NO:8)

Junc. Rub 1023r 5' AGATAGTAAATTCTCAAATGAATTC (SEQ ID NO:9)

DHSc125c 5' TTGACAGGTGGCTATAAG (SEQ ID NO:10)

DHSc498r 5' CGTTTCTGCATGAGGAGC (SEQ ID NO: 11)

And a wild type clone, pKitmus/RbscK-DH-3'nc #9, has been conserved for further manipulations (FIGS. 5A–5C).

The gene was put in a cassette for transient expression. Plasmid 35SC4PPDK-sGFP-TYG-nos was obtained from Jen Sheen at the Department of Molecular Biology at Massachusetts General Hospital and contains the following: the 35S-C4PPDK promoter flanked by XhoI and BamHI sites; a gene encoding GFP flanked by BamHI and PstI sites that contains an amino acid change at position 65 for increased fluorescence and whose codon usage is optimized for plant expression; and a polyadenylation sequence flanked by PstI and EcoRI sites. The BamHI site after the promoter was changed for a SphI site by a treatment of the vector digested BamHI with the Klenow and its ligation with a SphI linker. The vector produced was then digested EcoRI, treated with the Klenow and digested SphI to yield a SphI/blunt vector fragment of 3290 bp that has lost the gene GFP and the NOS. pKitmus/RbscK-DH-3'nc was digested SphI-SmaI and the 2198 bp fragment containing the dehydrogenase and the 3 'non coding region of alfalfa rubisco was ligated in the vector to produce pUC/35S.C4PPDK.DH.3'nc, a 5488 bp clone used in the transient expression experiment (FIGS. 5D–5E).

For plant expression, the cassette containing the alfalfa rubisco promoter, the dehydrogenase and the 3' non coding region of alfalfa rubisco was obtained by a SalI/SmaI digestion of pKitmus/RbscK-DH-3'nc #9 and cloned in pCambia 2300. The clone formed is called pCambia/RbscK-DH-3'nc (FIGS. 5F–5J).

Diagrams of the constructs are shown in FIG. 4, and the sequences files are found in FIGS. 5A–5J.

For the enzymatic activity of the (D)-3-hydroxyacyl-CoA dehydrogenase in E. coli, a 2XYT.Ap liquid culture (5 mL) is inoculated with a single colony of DH5α: pTRCN/FOX2 and the culture is placed under agitation at 30° C. for 16 hours. This overnight culture is used to innoculate (1%) 50 mL of 2XYT.Ap media. The cultures are put at 30° C. under agitation until the OD600 nm reach 0.6. IPTG (0.4 mM) is added and the culture is incubated for another 4 hours. The cells are collected by centrifugation (15 min./5000 g/4° C.) and stored at −80° C. The cells are resuspended in 20 mM $KH_2PO_4$ buffer (pH 7.0), 0.5 mM DTT, 0.1 mM PMSF and are disrupted by sonication with pulses of 0.2 sec for a total period of 20 sec. The cells are returned to ice for cooling purposes and the sonication procedure is repeated two more times to ensure lysis. The extract is clarified by centrifugation in a microfuge (12000 g/15 min./4° C.) prior to activity measurements.

The dehydrogenase reaction measured the oxidation of a 3-hydroxyacyl-CoA in a 3-ketoacyl-CoA and is followed by monitoring the formation of the $Mg^{2+}$ complex of 3-ketoacyl-CoA at 303 nm. The incubation mixture consisted of 50 μmol Tris-Ci (pH 9.0), 50 μg bovine serum albumin, 50 μmol KCl, 1 μmol $NAD^+$, 25 μmol $MgCl_2$, 1 μmol pyruvate and 10 μg lactate dehydrogenase in a total volume of 1 mL. The lactate dehydrogenase allows the regeneration of $NAD^+$ using the pyruvate as substrate. The reaction is monitored at room temperature with all the components of the incubation mixture and then 10 μg of L-3-hydroxyacyl-CoA dehydrogenase is added. After about 1 minute, 50 nmol of the substrate DL-3-hydroxyoctanoyl-CoA is added. When the $OD_{303nm}$ is stabilized, meaning that the L-3-hydroxyoctanoyl-CoA is completely oxidized, then the extract (1%) is added. The reaction is monitored for another 5 minutes.

Figure 6A:
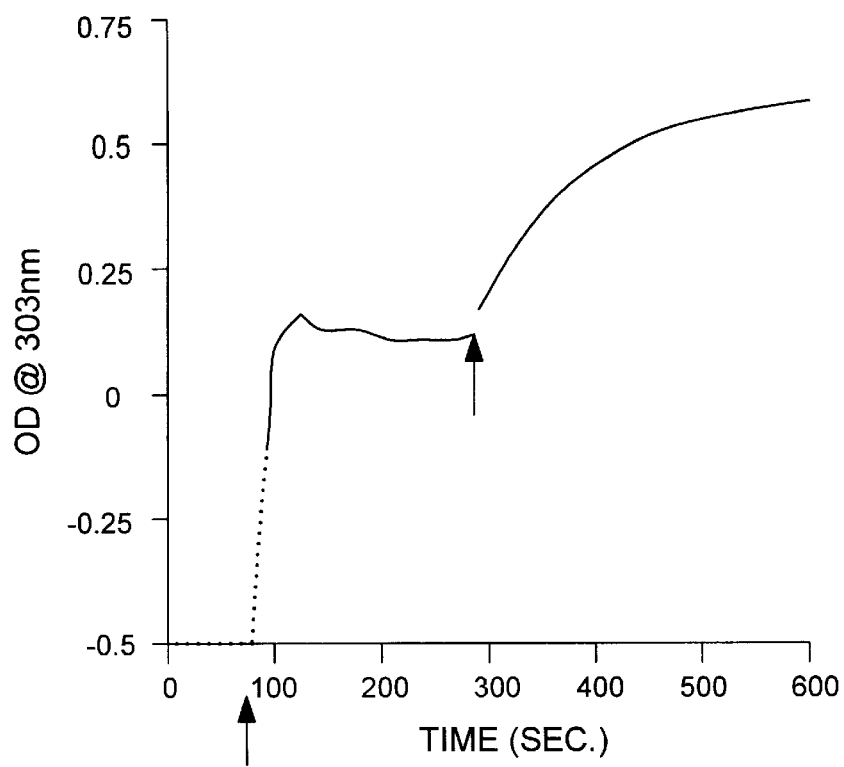
FIGS. 6A–6B show the dehydrogenase activity in *E.coli*. The monitoring activity is shown in FIG. 6A and the linear part of the graph that represents the D-3-hydrozyacyl-CoA dehydrogenase activity is shown in FIG. 6B.
Figure 6B:
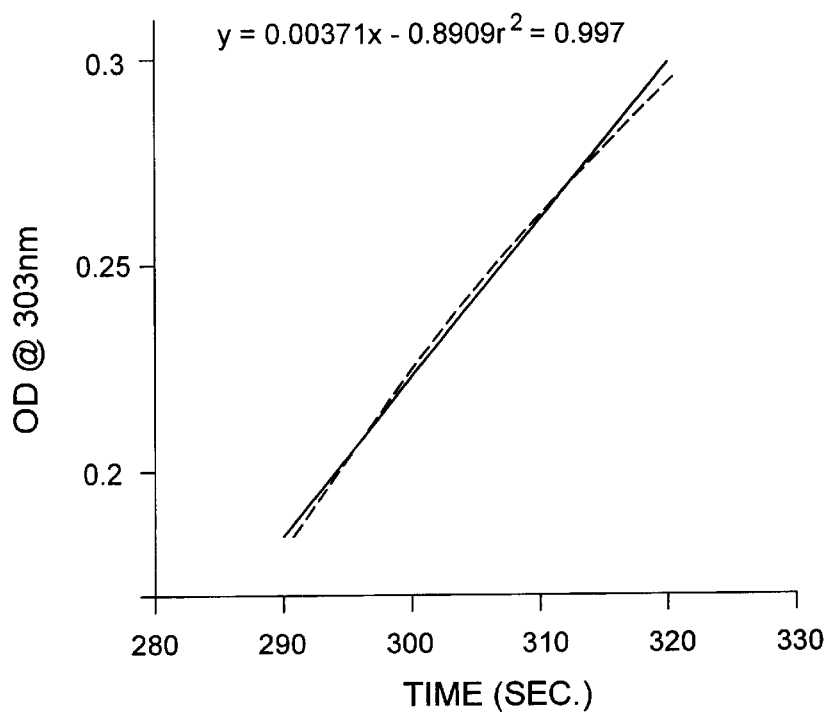

The R-3-hydroxyacyl-CoA dehydrogenase activity was measured in DH5α overexpression the MFP Fox2 gene of Saccharomyces cerevisiae. The extinction coefficient used for the 3-ketooctanoyl-CoA is $14.5 \times 10^3$ $cm^{-1}$ $M^{-1}$. The monitoring activity is shown on FIG. 6A and the linear part of the graph that represents the R-3-hydroxyacyl-CoA dehydrogenase activity is shown in FIG. 6B. The specific activity is 0.81 Units/mg protein.

Transient expression of the 3-hydroxyacyl-CoA dehydrogenase in plant cells was done by transformation of Arabidopsis thaliana protoplasts with pUC/35S.C4PPDK.DH.3'nc (Sheen, J., et al., 1995). For the enzymatic activity of the (D)-3-hydroxyacyl-CoA dehydrogenase in plant cells, Arabidopsis thaliana protoplasts are harvested by centrifugation (115 g) and the supernatant is removed. An aliquot (14 μL) of 7×stock of protease inhibitor stock is added to the sample and the sample is brought to a final volume of 100 μL with a solution containing 20 mM $KH_2PO_4$ buffer (pH 7.0), 0.5 mM DTT, 0.1 mM PMSF. The 7×stock of protease inhibitors is prepared by dissolving one "Complete Mini Protease Inhibitor Tablet" (Boehringer Mannheim) in 1.5 mL 20 mM $KH_2PO_4$ buffer (pH 7.0), 0.5 mM DTT, 0.1 mM PMSF. The protoplasts are disrupted in a 1.5 mL centrifuge tube using a pellet pestle mixer (Kontes) for 30 seconds. Soluble proteins are separated from insoluble proteins by centrifugation at maximum speed in a microcentrifuge (10 min, 4° C.). Dehydrogenase activity was measured as described above. The R-3-hydroxyacyl-CoA dehydrogenase activity was measured in protoplasts of Arabidopsis thaliana transformed with pUC/35S.C4PPDK.DH.3'nc. The extinction coefficient used for the 3-ketooctanoyl-CoA is $14.5 \times 10^3$ $cm^{-1}$ $M^{-1}$.

Arabidopsis thaliana plants were transformed with pCambia/RbscK-DH-3'nc following a floral dip protocol (Clough, S. J., et al. 1998) and using the Agrobacterium tumefasciens strain GV3101/pMP90 (Koncz, C., et al., 1986). For the enzymatic activity of the (D)-3-hydroxyacyl-CoA dehydrogenase in plants, leaves of Arabidopsis thaliana expressing the enzyme are collected and grinded in 5 volumes of extraction buffer containing 50 mM Tris-Cl buffer (pH 8.0), 0.4% β-mercaptoethanol, 2 mM PMSF. The extract is clarified on Miracloth and centrifuged (12 000g/15 min./4° C.). The supernatant is desalted on a Sephadex G-25 PD-10 column (Pharmacia) eluting in a buffer containing 20 mM $KH_2PO_4$ buffer (pH 7.0), 0.5 mM DTT, 0.1 mM PMSF. Dehydrogenase activity was determined as described above. The R-3-hydroxyacyl-CoA dehydrogenase activity was measured in plants of Arabidopsis thaliana transformed with pCambia/RbscK-DH-3'nc. The extinction coefficient used for the 3-ketooctanoyl-CoA is $14.5 \times 10^3$ $cm^{-1}$ $M^{-1}$.

Keto-acyl CoA thiolase

Cloning of the thiolase gene (X93015) (Olesen, 1997) was performed by PCR amplification of genomic DNA from Brassica napus as described above, except that the annealing temperature used was 50° C. Template DNA was prepared from B. napus leaves as described by Rogers & Bendich, Plant Mol. Biol., 1988, A6:1–10. The primer at the 5' end was 5'GATCGCATGCTAGCTGGGGACAGTGCTGCGTATC-3' (SEQ ID NO:12) with an added SphI site, and at the 3' end 5'-GATCGAATTCCTAACGAGCGTCCTTGGACAAAAG-3' (SEQ ID NO:13) with an EcoRI site downstream of the stop codon. Primers were selected so that amplification would be initiated at position 106 of the cDNA and therefore eliminate the N-terminal targeting signal for glyoxysomes. The gel-purified PCR products were digested with SphI/EcoRI and cloned in a derivative of pLitmus 28 modified as described above for cloning of yeast dehydrogenase. Suitable clones are fully sequenced. Sequence was compared with the published cDNA (1389 pb), although amplicons were produced from genomic DNA template. Homologous amplicons with introns and without the targeting signal are 2568-bp in size. The whole construct with the homologous gene was sub-cloned at the SalI/SmaI site in pBI 101.2. Transformation of A. tumefaciens, transformation of selected plants, and regeneration of transgenic lines was performed as described above. Selection of best transgenic lines was performed with Northern hybridization.

Acyl-ACP Thioesterase

A gene encoding for a thioesterase with specificity for 8:0 and 10:0-ACP substrates (U39834) (Dehesh, 1996) was amplified by PCR from Cuphea hookeriana as described above, except that the annealing temperature used was 60° C. Template genomic DNA was prepared with the Qiagen Genomic Tip Protocol as described by the manufacturer. The primer at the 5' end was 5'-GATCTCTAGAATGGTGGCTGCTGCAGCAAGTTCCG-3' (SEQ ID NO:14) with a XbaI site upstream of the ATG; the primer at the 3' end was 5'-GATCGGGCCCCTAAGAGACCGAGTTTCCATTTGAAG-3' (SEQ ID NO:15) with an ApaI site downstream of the stop codon. The PCR product was cloned at the XbaI/ApaI site in the plant vector pCambia 2300, modified to harbor the RbscK promotor (SalI/SphI) with the transit peptide, a multiple cloning site between SphI and EcoRI and the 3' non coding region of RbscK (EcoRI/SmaI). Transformation of *A. tumefaciens*, transformation of selected plants, and regeneration of transgenic lines was performed as described above. Selection of best transgenic lines was performed with Northern hybridization.

Acyl-CoA Synthetase

Cloning of the acyl-CoA synthetase gene (X65936) (van Beilen, 1992) was performed by PCR amplification of genomic DNA from *Pseudomonas oleovorans*. Template DNA was prepared as described in Current Protocols in Molecular Biology, 1997, 2.4.1–2.4.2. The primer at the 5'-end was GATC GGATCCATGTTAGGTCAGATGATGCGT-3' (SEQ ID NO:16) with a BamHI site upstream of the ATG; the primer at the 3' end was 5'-GATC GAATTCTTATTCACAGACAGAAGAACT-3' (SEQ ID NO:17) with an EcoRI site downstream of the stop codon. The PCR product was cloned in the BamHI/EcoRI site of pLitmus 28 modified as described above for cloning of yeast dehydrogenase. Suitable clones were fully sequenced. Wjole constructs were then sub-cloned into pBI.101.2. Transformation of *A. tumefaciens*, transformation of alfalfa and tobacco plants, and regeneration of transgenic lines was performed as described above. Selection of best transgenic lines was performed with Northern hybridization.

All scientific references and patent documents are incorporated herein by reference.

The invention as herein described can be varied in many ways. Such variations are not to be regarded as a departure from the spirit and scope of the present invention. All modifications as would be obvious to one skilled in the art are intended to be included within the scope of the following claims.

REFERENCES

Anderson, A. J. & Dawes, E. A. (1990) Occurrence, metabolism, metabolic role, and industrial uses of bacterial polyhydroxyalkanoates. *Microbiology Review* 54: 450–472.

Barham, P. J., Keller, A., Otun, E. L. & Holmes, P. A. (1984) Crystallization and morphology of a bacterial thermoplastic: poly-3-hydroxybutyrate. *J. Mat. Sci.* 19: 2781–2794.

Byrom, D. (1994) Polyhydroxyalkanoates. In *Plastics from microbes: microbial synthesis of polymers and polymers precursors*, Vol. eds D. P. Mobley, pp. 5–33. Munich: Hanser.

Clough, S. J., Bent, A. F. Floral dip: a simplified method for Agrobacterium-mediated transformation of *Arabidopsis thaliana*. The Plant Journal (1998) 16 (6), 735–743.

De Koning, G. J. M., Lemstra, P. J., Hill, D. J. T., Carswell, T. G. & O'Donnell, J. H. (1992) Ageing phenomena in bacterial poly(R)-3-hydroxybutyrate. *Polymer* 33: 3295–3297.

De Koning, G. J. M., van Bilsen, H. M. M., Lemstra, P. J., Hazenberg, W., Witholt, B., Preusting, H., van der Galien, J. G., Schirmer, A. & Jendrossek, D. (1994) A biodegradable rubber by cross linking poly(hydroxyalkanoates) from *Pseudomonas oleovorans*. *Polymer* 35: 2090–2097.

de Lorenzo, V. & Timmis, K. N. (1994) Analysis and construction of stable phenotypes in gram-negative bacteria with Tn5- and Tn10-derived minitransposons. In *Methods in enzymology; Genetics and regulation*, Vol. 235, p. 386. New York: Academic Press Inc.

Doi, Y. (1990) *Microbial polyesters*. New York: VCH.

Doi, Y., Segawa, A. & Kunioka, M. (1990) BiodegBiosynthesis and characterization of poly(3-hydroxybutyrate-co-4-hydroxybutyrate) in *Alcaligenes eutrophus*. *Int. J. Biol. Macromol.* 12: 101–111.

Gagnon, K. D., Lenz, R. W., Farris, R. J. & Fuller, R. C. (1992) The mechanical properties of a thermoplastic elastomer produced by the bacterium *Pseudomonas oleovorans*. *Rubber Chem. Technol.* 65: 761–777.

Gross, R. A., DeMello, C., Lenz, R. W., Brandl, H. & Fuller, R. C. (1989) Biosynthesis and characterization of poly(β-hydroxyalkanoates) produced by *Pseudomonas oleovorans*. *Macromolecules* 22: 1106–1115.

Hahn, J. J., T. A. Leaf, A. C. Eschenlauer, D. A. Somers & F. Srienc (1996) Peroxisomal localization of PHA synthesis in eukaryotic cells. *International symposium on bacterial polyhydroxyalkanoates'96*. Davos, Switzerland, Aug. 18–23, 1996.

Hiltunen, J. K., Wenzel, B., Beyer, A., Erdmann, R., Fossa, A., Junau, W. H., (1992) Peroxisomal multifunctional b-oxidation protein of *Saccharomyces cerevisiae*, J. Biol. Chem. 267, 6646–6653)

Holmes, P. A. (1988) Biologically produced PHA polymers and copolymers. In *Developments in crystalline polymers*, Vol. 2, eds D. C. Bassett, pp. 1–65. London: Elsevier.

Huijberts, G. N. M., Eggink, G., de Waard, P., Huisman, G. W. & Witholt, B. (1992) *Pseudomonas putida* KT2442 cultivated on glucose accumulates poly(3-hydroxyalkanoates) consisting of saturated and unsaturated monomers. *Appl. Environ. Microbiol.* 58: 536–544.

Huijberts, G. N. M., de Rijk, T. C., de Waard, P. & Eggink, G. (1994) 13C Nuclear mAgnetic resonance studies of *Pseudomonas putida* fatty acid metabolic routes involved in poly(3-hydroxyalkanoates) synthesis. *J. Bacteriol.* 176: 16661–1666.

Huisman, G. W. (1991) *Poly(3-hydroxyalkanoates) from Pseudomonas putida: from DNA to plastic*. Ph.D., Groningen University, The Netherlands.

Koncz, C., Schell, J., The promoter of $T_L$-DNA gene 5 controls the tissue-specific expression of chimeric genes carried by a novel type of Agrobacterium binary vector. Mol. Gen. Genet. (1986) 204: 383–396.

Kumagai, Y. & Doi, Y. (1992a) Enzymatic degradation of poly(3-hydroxybutyrate)-based blends: poly(3-hydroxybutyrate)/poly(ethylene oxide) blend. *Polym. Degrad. Stab.* 35: 87–93.

Kumagai, Y. & Doi, Y. (1992b) Enzymatic degradation and morphologies of binary blends of microbial poly(3-hydroxybutyrate) and poly(caprolactone), poly(1,4-butylene adipate) and poly(vinyl acetate). *Polym. Degrad. Stab.* 36: 241–248.

Kumagai, Y. & Doi, Y. (1992c) Physical properties and biodegradability of blends of isotactic and atactic poly(3-hydroxybutyrate). *Makromol. Chem. Rapid Commun.* 13: 179–183.

Law, J. H. & Slepecky, R. A. (1961) Assay of poly-β-hydroxybutyric acid. *J. Bacteriol.* 82: 33.

Lee, S. Y. (1996) Bacterial polyhydroxyalkanoates. *Biotechnology and Bioengineering* 49: 1–14.

Liebergessel, M. & Steinbüchel, A. (1 993) Cloning and molecular analysis of the poly (3-hydroxybutyric acid) biosynthetic genes of *Thiocystis violacea*. *Appl. Microbiol. Biotechnol.* 38: 493–501.

Liebergesell, M., Mayer, F. & Steinbüchel, A. (1994) Analysis of polyhydroxyalkanoic acid- biosynthesis genes of anoxygenic phototrophic bacteria reveals synthesis of a polyester exhibiting an unusual composition. *Appl. Microbiol. Biotechnol.* 40: 292–300.

Lindsay, K. F. (1992) Truly degradable resins are now truly commercial. *Modern Plastics* 2: 62–64.

Nawrath, C., Poirier, Y. & Somerville, C. (1995) Plant polymers for biodegradable plastics: cellulose, starch and polyhydroxyalkanoates. *Molecular Breeding* 1: 105–122.

Nawrath, C., Poirier, Y. & Sommerville, C. (1994) Targeting of the polyhydroxybutyrate biosynthesis pathway to the plastids of *Arabidopsis thaliana* results in high-levels of polymer accumulation. *Natl. Acad. Sci. USA* 91: 12760–12764.

Pearce, R. & Marchessault, R. H. (1994) Multiple melting in blends of isotactic and atactic poly(3-hydroxybutyrate). *Polymer* 35: 3990–3997.

Poirier, Y., Dennis, D. E., Klomparens, K. & Somerville, C. (1992) Polyhydroxybutyrate, a biodegradable thermoplastic, produced in transgenic plants. *Science* 256: 520–523.

Poirier, Y., Nawrath, C. & Somerville, C. (1995) Production of polyhydroxyalkanoates, a family of biodegradable plastics and elastomers, in bacteria and plants. *Bio/technology* 13: 142–150.

Preusting, H., Nijenhuis, A. & Witholt, B. (1990) Physical characteristics of poly(3-hydroxyalkanoates) and poly(3-hydroxyalkenoates) produced by *Pseudomonas oleovorans* grown on aliphatic hydrocarbons. *Macromolecules* 23: 4220–4224.

Rangan, V. S. & Smith, S. (1997) Alteration of the substrate specificity of the malonyl-CoA/acetyl-CoA:acyl carrier protein S-acyltransferase domain of the multifunctional fatty acid synthase by mutation of a single arginine residue. *J. Biol. Chem.* 272(18): 11975–11978.

Schlegel, H. G., Kaltwasser, H. & Gottschalk, G. (1961) Ein submersverfahren zur kultur wasserstoffoxydierender bakterien: wachstumsphysiologische untersuchungen. *Arch. Mikrobiol.* 38: 209–222.

Schubert, P., Steinbüchel, A. & Schlegel, H. G. (1988) Cloning of the *Alcaligenes eutrophus* genes for synthesis of poly-β-hydroxybutyric acid (PHB) and synthesis of PHB in *Escherichia coli. J Bacteriol.* 170(12): 5837–5847.

Sheen, J., Hwang, S., Niwa, Y., Kobayashi, H. and Galbraith, D. W. Green-fluorescent protein as a new vital marker in plant cells. The Plant Journal (1995) 8(5), 777–784

Sherman, D. H. (1996). A combinatorial biology approach to PHAacy synthesis. *International symposium on bacterial polyhydroxyalkanoates'96*. Davos, Switzerland, Aug. 18–23, 1996.

Slater, S. C., Voige, W. H. & Dennis, D. E. (1988) Cloning and expression in *Escherichia coli* of the *Alcaligenes eutrophus* H16 poly-β-hydroxybutyrate biosynthetic pathway. *J. Bacteriol.* 170(10): 4431–4436.

Srienc, F. & T. Leaf(1996). *International symposium on bacterial polyhydroxyalkanoates'96*. Davos, Switzerland, Aug. 18–23, 1996.

Stadman, E. R. (1957) Preparation ans assay of acyl coenzyme A and other thiol esters; use of hydroxylamine. In *Methods in enzymology*, Vol. 3, eds S. P. Colowick & N. O. Kaplan, p. 931. New York: Academic Press, inc.

Steinbüchel, A. (1991) Polyhydroxyalkanoic acids. In *Biomaterials: novel materials from biological sources*, Vol. eds D. Byrom, pp. 124–213. New York: Stockton.

Steinbüchel, A., Hustede, E., Liebergesell, M., Pieper, U., Timm, A. & Valentin, H. (1992) Molecular basis for biosynthesis and accumulation of polyhydroxyalkanoic acids in bacteria. *FEMS Microbiol. Rev.* 103: 217–230.

Steinbüchel, A. & Schlegel, H. G. (1991) Physiology and molecular genetics of poly(β-hydroxyalkanoic acid) synthesis in *Alcaligenes eutrophus*. *Mol. Microbiol.* 5(3): 535–542.

Steinbüchel, A. & Valentin, H. E. (1995) Diversity of bacterial polyhydroxyalkanoic acids. *FEMS Microbiol. Lett.* 128: 219–228.

Timm, A. & Steinbüchel, A. (1990) Formation of polyesters consisting of medium-chain-length 3-hydroxyalkanoic acids from gluconate by *Pseudomonas aeruginosa* and other fluorescent pseudomonads. *Appl. Environ. Microbiol.* 56: 3360–3367.

Timm, A. & Steinbüchel, A. (1992) Cloning and molecular analysis of the poly(3-hydroxyalkanoic acid) gene locus of *Pseudomonas aeruginosa* PAO 1. *Eur. J. Appl. Microbiol.* 209: 15–30.

van der Leij, F. R. & Witholt, B. (1995) Strategies for the sustainable production of new biodegradable polyesters in plants: a review. *Can. J. Microbiol.* 41(Suppl. 1): 222–238.

Williams, S., Friedrich, L., Dincher, S., Carozzi, N., Kessmann, H., Ward, E. & Ryals, J. (1992) Chemical regulation of *Bacillus thuringiensis* d-endotoxin expression in transgenic plants. *Bio/technology* 10: 540–543.

What is claimed is:

1. A method for producing a polyhydroxyalkanoate in a host comprising:
   selecting a host for expression of genes encoding enzymes required for synthesis of a polyhydroxyalkanoate;
   introducing into said host structural genes encoding a thioesterase, an acyl-CoA synthetase, a thiolase, a yeast (R)-3-hydroxyacyl-CoA dehydrogenase, and a polyhydroxyalkanoate synthase;
   expressing the enzymes encoded by the genes; and
   providing the appropriate substrates for the expressed enzymes to synthesize the polyhydroxyalkanoate.

2. The method according to claim 1, wherein the host is a plant.

3. The method according to claim 1, wherein the plant is selected from the group consisting of potato, sweet potato, cassava, beet, alfalfa, Arabidopsis, and tobacco.

* * * * *

```
                        SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 705 base pairs
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..705

(ix) FEATURE:
```

(A) NAME/KEY: mat_peptide
        (B) LOCATION: 1..705

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AGG | GTC | CCC | GCT | CAG | CTC | CTG | GGG | CTC | CTG | CTG | CTC | TGG | CTC | CCA | 48 |
| Met | Arg | Val | Pro | Ala | Gln | Leu | Leu | Gly | Leu | Leu | Leu | Leu | Trp | Leu | Pro | |
| 1 | | | | 5 | | | | | 10 | | | | | 15 | | |
| GGT | GCA | CGA | TGT | GCC | TAT | GAA | CTG | ACT | CAG | CCA | CCC | TCG | GTG | TCA | GTG | 96 |
| Gly | Ala | Arg | Cys | Ala | Tyr | Glu | Leu | Thr | Gln | Pro | Pro | Ser | Val | Ser | Val | |
| | | | 20 | | | | | 25 | | | | | 30 | | | |
| TCC | CCA | GGA | CAG | ACG | GCC | AGG | ATC | ACC | TGT | GGG | GGA | GAC | AAC | AGT | AGA | 144 |
| Ser | Pro | Gly | Gln | Thr | Ala | Arg | Ile | Thr | Cys | Gly | Gly | Asp | Asn | Ser | Arg | |
| | | 35 | | | | | 40 | | | | | 45 | | | | |
| AAT | GAA | TAT | GTC | CAC | TGG | TAC | CAG | CAG | AAG | CCA | GCG | CGG | GCC | CCT | ATA | 192 |
| Asn | Glu | Tyr | Val | His | Trp | Tyr | Gln | Gln | Lys | Pro | Ala | Arg | Ala | Pro | Ile | |
| | 50 | | | | | 55 | | | | | 60 | | | | | |
| CTG | GTC | ATC | TAT | GAT | GAT | AGT | GAC | CGG | CCC | TCA | GGG | ATC | CCT | GAG | CGA | 240 |
| Leu | Val | Ile | Tyr | Asp | Asp | Ser | Asp | Arg | Pro | Ser | Gly | Ile | Pro | Glu | Arg | |
| 65 | | | | | 70 | | | | | 75 | | | | | 80 | |
| TTC | TCT | GGC | TCC | AAA | TCA | GGG | AAC | ACC | GCC | ACC | CTG | ACC | ATC | AAC | GGG | 288 |
| Phe | Ser | Gly | Ser | Lys | Ser | Gly | Asn | Thr | Ala | Thr | Leu | Thr | Ile | Asn | Gly | |
| | | | | 85 | | | | | 90 | | | | | 95 | | |
| GTC | GAG | GCC | GGG | GAT | GAG | GCT | GAC | TAT | TAC | TGT | CAG | GTG | TGG | GAC | AGG | 336 |
| Val | Glu | Ala | Gly | Asp | Glu | Ala | Asp | Tyr | Tyr | Cys | Gln | Val | Trp | Asp | Arg | |
| | | | 100 | | | | | 105 | | | | | 110 | | | |
| GCT | AGT | GAT | CAT | CCG | GTC | TTC | GGA | GGA | GGG | ACC | CGG | GTG | ACC | GTC | CTA | 384 |
| Ala | Ser | Asp | His | Pro | Val | Phe | Gly | Gly | Gly | Thr | Arg | Val | Thr | Val | Leu | |
| | | 115 | | | | | 120 | | | | | 125 | | | | |
| GGT | CAG | CCC | AAG | GCT | GCC | CCC | TCG | GTC | ACT | CTG | TTC | CCG | CCC | TCC | TCT | 432 |
| Gly | Gln | Pro | Lys | Ala | Ala | Pro | Ser | Val | Thr | Leu | Phe | Pro | Pro | Ser | Ser | |
| | 130 | | | | | 135 | | | | | 140 | | | | | |
| GAG | GAG | CTT | CAA | GCC | AAC | AAG | GCC | ACA | CTG | GTG | TGT | CTC | ATA | AGT | GAC | 480 |
| Glu | Glu | Leu | Gln | Ala | Asn | Lys | Ala | Thr | Leu | Val | Cys | Leu | Ile | Ser | Asp | |
| 145 | | | | | 150 | | | | | 155 | | | | | 160 | |
| TTC | TAC | CCG | GGA | GCC | GTG | ACA | GTG | GCC | TGG | AAG | GCA | GAT | AGC | AGC | CCC | 528 |
| Phe | Tyr | Pro | Gly | Ala | Val | Thr | Val | Ala | Trp | Lys | Ala | Asp | Ser | Ser | Pro | |
| | | | | 165 | | | | | 170 | | | | | 175 | | |
| GTC | AAG | GCG | GGA | GTG | GAG | ACC | ACC | ACA | CCC | TCC | AAA | CAA | AGC | AAC | AAC | 576 |
| Val | Lys | Ala | Gly | Val | Glu | Thr | Thr | Thr | Pro | Ser | Lys | Gln | Ser | Asn | Asn | |
| | | | 180 | | | | | 185 | | | | | 190 | | | |
| AAG | TAC | GCG | GCC | AGC | AGC | TAC | CTG | AGC | CTG | ACG | CCT | GAG | CAG | TGG | AAG | 624 |
| Lys | Tyr | Ala | Ala | Ser | Ser | Tyr | Leu | Ser | Leu | Thr | Pro | Glu | Gln | Trp | Lys | |
| | | 195 | | | | | 200 | | | | | 205 | | | | |
| TCC | CAC | AGA | AGC | TAC | AGC | TGC | CAG | GTC | ACG | CAT | GAA | GGG | AGC | ACC | GTG | 672 |
| Ser | His | Arg | Ser | Tyr | Ser | Cys | Gln | Val | Thr | His | Glu | Gly | Ser | Thr | Val | |
| | 210 | | | | | 215 | | | | | 220 | | | | | |
| GAG | AAG | ACA | GTG | GCC | CCT | ACA | GAA | TGT | TCA | TGA | | | | | | 705 |
| Glu | Lys | Thr | Val | Ala | Pro | Thr | Glu | Cys | Ser | * | | | | | | |
| 225 | | | | | 230 | | | | | 235 | | | | | | |

(2) INFORMATION FOR SEQ ID NO:2:

(i) SEQUENCE CHARACTERISTICS:
        (A) LENGTH: 234 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Val Pro Ala Gln Leu Leu Gly Leu Leu Leu Leu Trp Leu Pro
 1               5                  10                  15

```
Gly Ala Arg Cys Ala Tyr Glu Leu Thr Gln Pro Ser Val Ser Val
            20                  25                  30

Ser Pro Gly Gln Thr Ala Arg Ile Thr Cys Gly Gly Asp Asn Ser Arg
        35                  40                  45

Asn Glu Tyr Val His Trp Tyr Gln Gln Lys Pro Ala Arg Ala Pro Ile
    50                  55                  60

Leu Val Ile Tyr Asp Asp Ser Asp Arg Pro Ser Gly Ile Pro Glu Arg
65                  70                  75                  80

Phe Ser Gly Ser Lys Ser Gly Asn Thr Ala Thr Leu Thr Ile Asn Gly
                85                  90                  95

Val Glu Ala Gly Asp Glu Ala Asp Tyr Tyr Cys Gln Val Trp Asp Arg
            100                 105                 110

Ala Ser Asp His Pro Val Phe Gly Gly Gly Thr Arg Val Thr Val Leu
            115                 120                 125

Gly Gln Pro Lys Ala Ala Pro Ser Val Thr Leu Phe Pro Pro Ser Ser
        130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230                 235

(2) INFORMATION FOR SEQ ID NO:3:

(i) SEQUENCE CHARACTERISTICS:
        (A) LENGTH: 1430 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..1431

(ix) FEATURE:
        (A) NAME/KEY: mat_peptide
        (B) LOCATION: 1..1431

(xi) SEQUENCE DESCRIPTION: SEQ ID NO:3:

ATG AAA CAC CTG TGG TTC TTC CTC CTC CTG GTG GCA GCT CCC AGA TGG       48
Met Lys His Leu Trp Phe Phe Leu Leu Leu Val Ala Ala Pro Arg Trp
1               5                   10                  15

GTC CTG TCC CAG GTG AAG CTG CAG CAG TGG GGC GAA GGA CTT CTG CAG       96
Val Leu Ser Gln Val Lys Leu Gln Gln Trp Gly Glu Gly Leu Leu Gln
            20                  25                  30

CCT TCG GAG ACC CTG TCC CGC ACC TGC GTT GTC TCT GGT GGC TCC ATC      144
Pro Ser Glu Thr Leu Ser Arg Thr Cys Val Val Ser Gly Gly Ser Ile
        35                  40                  45

AGC GGT TAC TAC TAC TGG ACC TGG ATC CGC CAG ACC CCA GGG AGG GGA      192
Ser Gly Tyr Tyr Tyr Trp Thr Trp Ile Arg Gln Thr Pro Gly Arg Gly
    50                  55                  60
```

```
CTG GAG TGG ATT GGC CAT ATT TAT GGT AAT GGT GCG ACC ACC AAC TAC         240
Leu Glu Trp Ile Gly His Ile Tyr Gly Asn Gly Ala Thr Thr Asn Tyr
 65              70                  75                  80

AAT CCC TCC CTC AAG AGT CGA GTC ACC ATT TCA AAA GAC ACG TCC AAG         288
Asn Pro Ser Leu Lys Ser Arg Val Thr Ile Ser Lys Asp Thr Ser Lys
                     85                  90                  95

AAC CAG TTC TTC CTG AAC TTG AAT TCT GTG ACC GAC GCG GAC ACG GCC         336
Asn Gln Phe Phe Leu Asn Leu Asn Ser Val Thr Asp Ala Asp Thr Ala
                100                 105                 110

GTC TAT TAC TGT GCG AGA GGC CCT CGC CCT GAT TGC ACA ACC ATT TGT         384
Val Tyr Tyr Cys Ala Arg Gly Pro Arg Pro Asp Cys Thr Thr Ile Cys
            115                 120                 125

TAT GGC GGC TGG GTC GAT GTC TGG GGC CCG GGA GAC CTG GTC ACC GTC         432
Tyr Gly Gly Trp Val Asp Val Trp Gly Pro Gly Asp Leu Val Thr Val
130                 135                 140

TCC TCA GCT AGC ACC AAG GGC CCA TCG GTC TTC CCC CTG GCA CCC TCC         480
Ser Ser Ala Ser Thr Lys Gly Pro Ser Val Phe Pro Leu Ala Pro Ser
145                 150                 155                 160

TCC AAG AGC ACC TCT GGG GGC ACA GCG GCC CTG GGC TGC CTG GTC AAG         528
Ser Lys Ser Thr Ser Gly Gly Thr Ala Ala Leu Gly Cys Leu Val Lys
                165                 170                 175

GAC TAC TTC CCC GAA CCG GTG ACG GTG TCG TGG AAC TCA GGC GCC CTG         576
Asp Tyr Phe Pro Glu Pro Val Thr Val Ser Trp Asn Ser Gly Ala Leu
            180                 185                 190

ACC AGC GGC GTG CAC ACC TTC CCG GCT GTC CTA CAG TCC TCA GGA CTC         624
Thr Ser Gly Val His Thr Phe Pro Ala Val Leu Gln Ser Ser Gly Leu
            195                 200                 205

TAC TCC CTC AGC AGC GTG GTG ACC GTG CCC TCC AGC AGC TTG GGC ACC         672
Tyr Ser Leu Ser Ser Val Val Thr Val Pro Ser Ser Ser Leu Gly Thr
210                 215                 220

CAG ACC TAC ATC TGC AAC GTG AAT CAC AAG CCC AGC AAC ACC AAG GTG         720
Gln Thr Tyr Ile Cys Asn Val Asn His Lys Pro Ser Asn Thr Lys Val
225                 230                 235                 240

GAC AAG AAA GCA GAG CCC AAA TCT TGT GAC AAA ACT CAC ACA TGC CCA         768
Asp Lys Lys Ala Glu Pro Lys Ser Cys Asp Lys Thr His Thr Cys Pro
                245                 250                 255

CCG TGC CCA GCA CCT GAA CTC CTG GGG GGA CCG TCA GTC TTC CTC TTC         816
Pro Cys Pro Ala Pro Glu Leu Leu Gly Gly Pro Ser Val Phe Leu Phe
            260                 265                 270

CCC CCA AAA CCC AAG GAC ACC CTC ATG ATC TCC CGG ACC CCT GAG GTC         864
Pro Pro Lys Pro Lys Asp Thr Leu Met Ile Ser Arg Thr Pro Glu Val
            275                 280                 285

ACA TGC GTG GTG GTG GAC GTG AGC CAC GAA GAC CCT GAG GTC AAG TTC         912
Thr Cys Val Val Val Asp Val Ser His Glu Asp Pro Glu Val Lys Phe
            290                 295                 300

AAC TGG TAC GTG GAC GGC GTG GAG GTG CAT AAT GCC AAG ACA AAG CCG         960
Asn Trp Tyr Val Asp Gly Val Glu Val His Asn Ala Lys Thr Lys Pro
305                 310                 315                 320

CGG GAG GAG CAG TAC AAC AGC ACG TAC CGT GTG GTC AGC GTC CTC ACC        1008
Arg Glu Glu Gln Tyr Asn Ser Thr Tyr Arg Val Val Ser Val Leu Thr
                325                 330                 335

GTC CTG CAC CAG GAC TGG CTG AAT GGC AAG GAG TAC AAG TGC AAG GTC        1056
Val Leu His Gln Asp Trp Leu Asn Gly Lys Glu Tyr Lys Cys Lys Val
            340                 345                 350

TCC AAC AAA GCC CTC CCA GCC CCC ATC GAG AAA ACC ATC TCC AAA GCC        1104
Ser Asn Lys Ala Leu Pro Ala Pro Ile Glu Lys Thr Ile Ser Lys Ala
                355                 360                 365

AAA GGG CAG CCC CGA GAA CCA CAG GTG TAC ACC CTG CCC CCA TCC CGG        1152
Lys Gly Gln Pro Arg Glu Pro Gln Val Tyr Thr Leu Pro Pro Ser Arg
```

```
                    370                 375                 380
GAT GAG CTG ACC AAG AAC CAG GTC AGC CTG ACC TGC CTG GTC AAA GGC       1200
Asp Glu Leu Thr Lys Asn Gln Val Ser Leu Thr Cys Leu Val Lys Gly
385                 390                 395                 400

TTC TAT CCC AGC GAC ATC GCC GTG GAG TGG GAG AGC AAT GGG CAG CCG       1248
Phe Tyr Pro Ser Asp Ile Ala Val Glu Trp Glu Ser Asn Gly Gln Pro
                405                 410                 415

GAG AAC AAC TAC AAG ACC ACG CCT CCC GTG CTG GAC TCC GAC GGC TCC       1296
Glu Asn Asn Tyr Lys Thr Thr Pro Pro Val Leu Asp Ser Asp Gly Ser
            420                 425                 430

TTC TTC CTC TAC AGC AAG CTC ACC GTG GAC AAG AGC AGG TGG CAG CAG       1344
Phe Phe Leu Tyr Ser Lys Leu Thr Val Asp Lys Ser Arg Trp Gln Gln
        435                 440                 445

GGG AAC GTC TTC TCA TGC TCC GTG ATG CAT GAG GCT CTG CAC AAC CAC       1392
Gly Asn Val Phe Ser Cys Ser Val Met His Glu Ala Leu His Asn His
    450                 455                 460

TAC ACG CAG AAG AGC CTC TCC CTG TCT CCG GGT AAA TGA                   1431
Tyr Thr Gln Lys Ser Leu Ser Leu Ser Pro Gly Lys
465                 470                 475

(2) INFORMATION FOR SEQ ID NO:4:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:4:

Met Lys His Leu Trp Phe Phe Leu Leu Leu Val Ala Ala Pro Arg Trp
 1               5                  10                  15

Val Leu Ser Gln Val Lys Leu Gln Gln Trp Gly Glu Gly Leu Leu Gln
                20                  25                  30

Pro Ser Glu Thr Leu Ser Arg Thr Cys Val Val Ser Gly Gly Ser Ile
            35                  40                  45

Ser Gly Tyr Tyr Tyr Trp Thr Trp Ile Arg Gln Thr Pro Gly Arg Gly
    50                  55                  60

Leu Glu Trp Ile Gly His Ile Tyr Gly Asn Gly Ala Thr Thr Asn Tyr
65                  70                  75                  80

Asn Pro Ser Leu Lys Ser Arg Val Thr Ile Ser Lys Asp Thr Ser Lys
                85                  90                  95

Asn Gln Phe Phe Leu Asn Leu Asn Ser Val Thr Asp Ala Asp Thr Ala
            100                 105                 110

Val Tyr Tyr Cys Ala Arg Gly Pro Arg Pro Asp Cys Thr Thr Ile Cys
    115                 120                 125

Tyr Gly Gly Trp Val Asp Val Trp Gly Pro Gly Asp Leu Val Thr Val
130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220
```

```
Gln Thr Tyr Ile Cys Asn Val Asn His Lys Pro Ser Asn Thr Lys Val
225                 230                 235                 240

Asp Lys Lys Ala Glu Pro Lys Ser Cys Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys
465                 470                 475

(2) INFORMATION FOR SEQ ID NO:5:

(i) SEQUENCE CHARACTERISTICS:
        (A) LENGTH: 719 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..720

(ix) FEATURE:
        (A) NAME/KEY: mat_peptide
        (B) LOCATION: 1..720

(xi) SEQUENCE DESCRIPTION: SEQ ID NO:5:

ATG AGC CTC CCT GCT CAG CTC CTC GGG CTG CTA TTG CTC TGC GTC CCC      48
Met Ser Leu Pro Ala Gln Leu Leu Gly Leu Leu Leu Leu Cys Val Pro
1               5                   10                  15

GGG TCC AGT GGG GAA GTT GTG ATG ACT CAG TCT CCA CTG TCC CTT CCC      96
Gly Ser Ser Gly Glu Val Val Met Thr Gln Ser Pro Leu Ser Leu Pro
            20                  25                  30

ATC ACA CCT GGA GAG CCG GCC TCC ATC TCC TGT AGG TCT AGT CAA AGC     144
```

```
Ile Thr Pro Gly Glu Pro Ala Ser Ile Ser Cys Arg Ser Ser Gln Ser
         35                  40                  45

CTT AAA CAC AGT AAT GGA GAC ACC TTC CTG AGT TGG TAT CAG CAG AAG      192
Leu Lys His Ser Asn Gly Asp Thr Phe Leu Ser Trp Tyr Gln Gln Lys
     50                  55                  60

CCA GGC CAA CCT CCA AGG CTC CTG ATT TAT AAG GTT TCT AAC CGG GAC      240
Pro Gly Gln Pro Pro Arg Leu Leu Ile Tyr Lys Val Ser Asn Arg Asp
 65                  70                  75                  80

TCT GGG GTC CCA GAC AGA TTC AGC GGC AGT GGG GCA GGG ACA GAT TTC      288
Ser Gly Val Pro Asp Arg Phe Ser Gly Ser Gly Ala Gly Thr Asp Phe
                 85                  90                  95

ACA CTG AAA ATC AGC GCA GTG GAG GCT GAA GAT GTT GGG GTT TAT TTC      336
Thr Leu Lys Ile Ser Ala Val Glu Ala Glu Asp Val Gly Val Tyr Phe
             100                 105                 110

TGC GGG CAA GGT ACA AGG ACT CCT CCC ACT TTC GGC GGA GGG ACC AAG      384
Cys Gly Gln Gly Thr Arg Thr Pro Pro Thr Phe Gly Gly Gly Thr Lys
         115                 120                 125

GTG GAA ATC AAA CGT ACG GTG GCT GCA CCA TCT GTC TTC ATC TTC CCG      432
Val Glu Ile Lys Arg Thr Val Ala Ala Pro Ser Val Phe Ile Phe Pro
 130                 135                 140

CCA TCT GAT GAG CAG TTG AAA TCT GGA ACT GCC TCT GTT GTG TGC CTG      480
Pro Ser Asp Glu Gln Leu Lys Ser Gly Thr Ala Ser Val Val Cys Leu
145                 150                 155                 160

CTG AAT AAC TTC TAT CCC AGA GAG GCC AAA GTA CAG TGG AAG GTG GAT      528
Leu Asn Asn Phe Tyr Pro Arg Glu Ala Lys Val Gln Trp Lys Val Asp
                 165                 170                 175

AAC GCC CTC CAA TCG GGT AAC TCC CAG GAG AGT GTC ACA GAG CAG GAC      576
Asn Ala Leu Gln Ser Gly Asn Ser Gln Glu Ser Val Thr Glu Gln Asp
             180                 185                 190

AGC AAG GAC AGC ACC TAC AGC CTC AGC AGC ACC CTG ACG CTG AGC AAA      624
Ser Lys Asp Ser Thr Tyr Ser Leu Ser Ser Thr Leu Thr Leu Ser Lys
         195                 200                 205

GCA GAC TAC GAG AAA CAC AAA GTC TAC GCC TGC GAA GTC ACC CAT CAG      672
Ala Asp Tyr Glu Lys His Lys Val Tyr Ala Cys Glu Val Thr His Gln
 210                 215                 220

GGC CTG AGC TCG CCC GTC ACA AAG AGC TTC AAC AGG GGA GAG TGT TGA      720
Gly Leu Ser Ser Pro Val Thr Lys Ser Phe Asn Arg Gly Glu Cys
225                 230                 235                 240
```

(2) INFORMATION FOR SEQ ID NO:6:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Leu Pro Ala Gln Leu Leu Gly Leu Leu Leu Leu Cys Val Pro
 1               5                  10                  15

Gly Ser Ser Gly Glu Val Val Met Thr Gln Ser Pro Leu Ser Leu Pro
                 20                  25                  30

Ile Thr Pro Gly Glu Pro Ala Ser Ile Ser Cys Arg Ser Ser Gln Ser
         35                  40                  45

Leu Lys His Ser Asn Gly Asp Thr Phe Leu Ser Trp Tyr Gln Gln Lys
     50                  55                  60

Pro Gly Gln Pro Pro Arg Leu Leu Ile Tyr Lys Val Ser Asn Arg Asp
 65                  70                  75                  80

Ser Gly Val Pro Asp Arg Phe Ser Gly Ser Gly Ala Gly Thr Asp Phe
```

```
                       85                  90                  95
Thr Leu Lys Ile Ser Ala Val Glu Ala Glu Asp Val Gly Val Tyr Phe
                100                 105                 110
Cys Gly Gln Gly Thr Arg Thr Pro Pro Thr Phe Gly Gly Gly Thr Lys
            115                 120                 125
Val Glu Ile Lys Arg Thr Val Ala Ala Pro Ser Val Phe Ile Phe Pro
    130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
                195                 200                 205
Ala Asp Tyr Glu Lys His Lys Val Tyr Ala Cys Glu Val Thr His Gln
    210                 215                 220
Gly Leu Ser Ser Pro Val Thr Lys Ser Phe Asn Arg Gly Glu Cys
225                 230                 235                 240

(2) INFORMATION FOR SEQ ID NO:7:

(i) SEQUENCE CHARACTERISTICS:
        (A) LENGTH: 1436 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..1437

(ix) FEATURE:
        (A) NAME/KEY: mat_peptide
        (B) LOCATION: 1..1437

(xi) SEQUENCE DESCRIPTION: SEQ ID NO:7:

ATG GGT TGG AGC CTC ATC TTG CTC TTC CTT GTC GCT GTT GCT ACG CGT        48
Met Gly Trp Ser Leu Ile Leu Leu Phe Leu Val Ala Val Ala Thr Arg
 1               5                  10                  15

GTC CAG TGT GAG GTG CAA CTG GTG GAG TCT GGG GGA GGC TTG GTC CAG        96
Val Gln Cys Glu Val Gln Leu Val Glu Ser Gly Gly Gly Leu Val Gln
            20                  25                  30

CCT GGC GGG TCC CTG AGA GTC TCC TGT GCA GTC TCT GGA TTC ACC TTC       144
Pro Gly Gly Ser Leu Arg Val Ser Cys Ala Val Ser Gly Phe Thr Phe
        35                  40                  45

AGT GAC CAC TAC ATG TAT TGG TTC CGC CAG GCT CCA GGG AAG GGG CCG       192
Ser Asp His Tyr Met Tyr Trp Phe Arg Gln Ala Pro Gly Lys Gly Pro
    50                  55                  60

GAA TGG GTA GGT TTC ATT AGA AAC AAA CCG AAC GGT GGG ACA ACA GAA       240
Glu Trp Val Gly Phe Ile Arg Asn Lys Pro Asn Gly Gly Thr Thr Glu
65                  70                  75                  80

TAC GCC GCG TCT GTG AAA GAC AGA TTC ACC ATC TCC AGA GAT GAT TCC       288
Tyr Ala Ala Ser Val Lys Asp Arg Phe Thr Ile Ser Arg Asp Asp Ser
                85                  90                  95

AAA AGC ATC GCC TAT CTG CAA ATG AGC AGC CTG AAA ATC GAG GAC ACG       336
Lys Ser Ile Ala Tyr Leu Gln Met Ser Ser Leu Lys Ile Glu Asp Thr
            100                 105                 110

GCC GTC TAT TAC TGT ACT ACA TCC TAC ATT TCA CAT TGT CGG GGT GGT       384
```

-continued

```
                    Ala Val Tyr Tyr Cys Thr Thr Ser Tyr Ile Ser His Cys Arg Gly Gly
                                115                 120                 125

GTC TGC TAT GGA GGT TAC TTC GAA TTC TGG GGC CAG GGC GCC CTG GTC                  432
Val Cys Tyr Gly Gly Tyr Phe Glu Phe Trp Gly Gln Gly Ala Leu Val
        130                 135                 140

ACC GTC TCC TCA GCT AGC ACC AAG GGC CCA TCG GTC TTC CCC CTG GCA                  480
Thr Val Ser Ser Ala Ser Thr Lys Gly Pro Ser Val Phe Pro Leu Ala
145                 150                 155                 160

CCC TCC TCC AAG AGC ACC TCT GGG GGC ACA GCG GCC CTG GGC TGC CTG                  528
Pro Ser Ser Lys Ser Thr Ser Gly Gly Thr Ala Ala Leu Gly Cys Leu
                165                 170                 175

GTC AAG GAC TAC TTC CCC GAA CCG GTG ACG GTG TCG TGG AAC TCA GGC                  576
Val Lys Asp Tyr Phe Pro Glu Pro Val Thr Val Ser Trp Asn Ser Gly
            180                 185                 190

GCC CTG ACC AGC GGC GTG CAC ACC TTC CCG GCT GTC CTA CAG TCC TCA                  624
Ala Leu Thr Ser Gly Val His Thr Phe Pro Ala Val Leu Gln Ser Ser
        195                 200                 205

GGA CTC TAC TCC CTC AGC AGC GTG GTG ACC GTG CCC TCC AGC AGC TTG                  672
Gly Leu Tyr Ser Leu Ser Ser Val Val Thr Val Pro Ser Ser Ser Leu
    210                 215                 220

GGC ACC CAG ACC TAC ATC TGC AAC GTG AAT CAC AAG CCC AGC AAC ACC                  720
Gly Thr Gln Thr Tyr Ile Cys Asn Val Asn His Lys Pro Ser Asn Thr
225                 230                 235                 240

AAG GTG GAC AAG AAA GCA GAG CCC AAA TCT TGT GAC AAA ACT CAC ACA                  768
Lys Val Asp Lys Lys Ala Glu Pro Lys Ser Cys Asp Lys Thr His Thr
                245                 250                 255

TGC CCA CCG TGC CCA GCA CCT GAA CTC CTG GGG GGA CCG TCA GTC TTC                  816
Cys Pro Pro Cys Pro Ala Pro Glu Leu Leu Gly Gly Pro Ser Val Phe
            260                 265                 270

CTC TTC CCC CCA AAA CCC AAG GAC ACC CTC ATG ATC TCC CGG ACC CCT                  864
Leu Phe Pro Pro Lys Pro Lys Asp Thr Leu Met Ile Ser Arg Thr Pro
        275                 280                 285

GAG GTC ACA TGC GTG GTG GTG GAC GTG AGC CAC GAA GAC CCT GAG GTC                  912
Glu Val Thr Cys Val Val Val Asp Val Ser His Glu Asp Pro Glu Val
    290                 295                 300

AAG TTC AAC TGG TAC GTG GAC GGC GTG GAG GTG CAT AAT GCC AAG ACA                  960
Lys Phe Asn Trp Tyr Val Asp Gly Val Glu Val His Asn Ala Lys Thr
305                 310                 315                 320

AAG CCG CGG GAG GAG CAG TAC AAC AGC ACG TAC CGT GTG GTC AGC GTC                 1008
Lys Pro Arg Glu Glu Gln Tyr Asn Ser Thr Tyr Arg Val Val Ser Val
                325                 330                 335

CTC ACC GTC CTG CAC CAG GAC TGG CTG AAT GGC AAG GAG TAC AAG TGC                 1056
Leu Thr Val Leu His Gln Asp Trp Leu Asn Gly Lys Glu Tyr Lys Cys
            340                 345                 350

AAG GTC TCC AAC AAA GCC CTC CCA GCC CCC ATC GAG AAA ACC ATC TCC                 1104
Lys Val Ser Asn Lys Ala Leu Pro Ala Pro Ile Glu Lys Thr Ile Ser
        355                 360                 365

AAA GCC AAA GGG CAG CCC CGA GAA CCA CAG GTG TAC ACC CTG CCC CCA                 1152
Lys Ala Lys Gly Gln Pro Arg Glu Pro Gln Val Tyr Thr Leu Pro Pro
    370                 375                 380

TCC CGG GAT GAG CTG ACC AAG AAC CAG GTC AGC CTG ACC TGC CTG GTC                 1200
Ser Arg Asp Glu Leu Thr Lys Asn Gln Val Ser Leu Thr Cys Leu Val
385                 390                 395                 400

AAA GGC TTC TAT CCC AGC GAC ATC GCC GTG GAG TGG GAG AGC AAT GGG                 1248
Lys Gly Phe Tyr Pro Ser Asp Ile Ala Val Glu Trp Glu Ser Asn Gly
                405                 410                 415

CAG CCG GAG AAC AAC TAC AAG ACC ACG CCT CCC GTG CTG GAC TCC GAC                 1296
Gln Pro Glu Asn Asn Tyr Lys Thr Thr Pro Pro Val Leu Asp Ser Asp
            420                 425                 430
```

```
GGC TCC TTC TTC CTC TAC AGC AAG CTC ACC GTG GAC AAG AGC AGG TGG    1344
Gly Ser Phe Phe Leu Tyr Ser Lys Leu Thr Val Asp Lys Ser Arg Trp
            435                 440                 445

CAG CAG GGG AAC GTC TTC TCA TGC TCC GTG ATG CAT GAG GCT CTG CAC    1392
Gln Gln Gly Asn Val Phe Ser Cys Ser Val Met His Glu Ala Leu His
        450                 455                 460

AAC CAC TAC ACG CAG AAG AGC CTC TCC CTG TCT CCG GGT AAA TGA        1437
Asn His Tyr Thr Gln Lys Ser Leu Ser Leu Ser Pro Gly Lys
465                 470                 475
```

(2) INFORMATION FOR SEQ ID NO:8:

(i) SEQUENCE CHARACTERISTICS:
        (A) LENGTH: 478 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Trp Ser Leu Ile Leu Leu Phe Leu Val Ala Val Ala Thr Arg
 1               5                  10                  15

Val Gln Cys Glu Val Gln Leu Val Glu Ser Gly Gly Gly Leu Val Gln
                20                  25                  30

Pro Gly Gly Ser Leu Arg Val Ser Cys Ala Val Ser Gly Phe Thr Phe
            35                  40                  45

Ser Asp His Tyr Met Tyr Trp Phe Arg Gln Ala Pro Gly Lys Gly Pro
        50                  55                  60

Glu Trp Val Gly Phe Ile Arg Asn Lys Pro Asn Gly Gly Thr Thr Glu
65                  70                  75                  80

Tyr Ala Ala Ser Val Lys Asp Arg Phe Thr Ile Ser Arg Asp Asp Ser
                85                  90                  95

Lys Ser Ile Ala Tyr Leu Gln Met Ser Ser Leu Lys Ile Glu Asp Thr
            100                 105                 110

Ala Val Tyr Tyr Cys Thr Thr Ser Tyr Ile Ser His Cys Arg Gly Gly
        115                 120                 125

Val Cys Tyr Gly Gly Tyr Phe Glu Phe Trp Gly Gln Gly Ala Leu Val
    130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Ile Cys Asn Val Asn His Lys Pro Ser Asn Thr
225                 230                 235                 240

Lys Val Asp Lys Lys Ala Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
```

```
                290                 295                 300
Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
                340                 345                 350

Lys Val Ser Asn Lys Ala Leu Pro Ala Pro Ile Glu Lys Thr Ile Ser
                355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
                420                 425                 430

Gly Ser Phe Phe Leu Tyr Ser Lys Leu Thr Val Asp Lys Ser Arg Trp
                435                 440                 445

Gln Gln Gly Asn Val Phe Ser Cys Ser Val Met His Glu Ala Leu His
                450                 455                 460

Asn His Tyr Thr Gln Lys Ser Leu Ser Leu Ser Pro Gly Lys
465                 470                 475

(2) INFORMATION FOR SEQ ID NO:9:

(i) SEQUENCE CHARACTERISTICS:
        (A) LENGTH: 710 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..711

(ix) FEATURE:
        (A) NAME/KEY: mat_peptide
        (B) LOCATION: 1..711

(xi) SEQUENCE DESCRIPTION: SEQ ID NO:9:

ATG AGG GTC CCC GCT CAG CTC CTG GGG CTC CTG CTG CTC TGG CTC CCA       48
Met Arg Val Pro Ala Gln Leu Leu Gly Leu Leu Leu Leu Trp Leu Pro
 1               5                  10                  15

GGT GCA CGA TGT GAG TCT GTC CTG ACA CAG CCG CCC TCA GTG TCT GGG       96
Gly Ala Arg Cys Glu Ser Val Leu Thr Gln Pro Pro Ser Val Ser Gly
            20                  25                  30

GCC CCA GGG CAG AAG GTC ACC ATC TCG TGC ACT GGG AGC ACC TCC AAC      144
Ala Pro Gly Gln Lys Val Thr Ile Ser Cys Thr Gly Ser Thr Ser Asn
        35                  40                  45

ATT GGA GGT TAT GAT CTA CAT TGG TAC CAG CAG CTC CCA GGA ACG GCC      192
Ile Gly Gly Tyr Asp Leu His Trp Tyr Gln Gln Leu Pro Gly Thr Ala
    50                  55                  60

CCC AAA CTC CTC ATC TAT GAC ATT AAC AAG CGA CCC TCA GGA ATT TCT      240
Pro Lys Leu Leu Ile Tyr Asp Ile Asn Lys Arg Pro Ser Gly Ile Ser
65                  70                  75                  80

GAC CGA TTC TCT GGC TCC AAG TCT GGT ACC GCG GCC TCC CTG GCC ATC      288
Asp Arg Phe Ser Gly Ser Lys Ser Gly Thr Ala Ala Ser Leu Ala Ile
                85                  90                  95
```

```
ACT GGG CTC CAG ACT GAG GAT GAG GCT GAT TAT TAC TGC CAG TCC TAT      336
Thr Gly Leu Gln Thr Glu Asp Glu Ala Asp Tyr Tyr Cys Gln Ser Tyr
            100                 105                 110

GAC AGC AGC CTG AAT GCT CAG GTA TTC GGA GGA GGG ACC CGG CTG ACC      384
Asp Ser Ser Leu Asn Ala Gln Val Phe Gly Gly Gly Thr Arg Leu Thr
        115                 120                 125

GTC CTA GGT CAG CCC AAG GCT GCC CCC TCG GTC ACT CTG TTC CCG CCC      432
Val Leu Gly Gln Pro Lys Ala Ala Pro Ser Val Thr Leu Phe Pro Pro
    130                 135                 140

TCC TCT GAG GAG CTT CAA GCC AAC AAG GCC ACA CTG GTG TGT CTC ATA      480
Ser Ser Glu Glu Leu Gln Ala Asn Lys Ala Thr Leu Val Cys Leu Ile
145                 150                 155                 160

AGT GAC TTC TAC CCG GGA GCC GTG ACA GTG GCC TGG AAG GCA GAT AGC      528
Ser Asp Phe Tyr Pro Gly Ala Val Thr Val Ala Trp Lys Ala Asp Ser
                165                 170                 175

AGC CCC GTC AAG GCG GGA GTG GAG ACC ACC ACA CCC TCC AAA CAA AGC      576
Ser Pro Val Lys Ala Gly Val Glu Thr Thr Thr Pro Ser Lys Gln Ser
            180                 185                 190

AAC AAC AAG TAC GCG GCC AGC AGC TAC CTG AGC CTG ACG CCT GAG CAG      624
Asn Asn Lys Tyr Ala Ala Ser Ser Tyr Leu Ser Leu Thr Pro Glu Gln
        195                 200                 205

TGG AAG TCC CAC AGA AGC TAC AGC TGC CAG GTC ACG CAT GAA GGG AGC      672
Trp Lys Ser His Arg Ser Tyr Ser Cys Gln Val Thr His Glu Gly Ser
    210                 215                 220

ACC GTG GAG AAG ACA GTG GCC CCT ACA GAA TGT TCA TGA                  711
Thr Val Glu Lys Thr Val Ala Pro Thr Glu Cys Ser
225                 230                 235
```

(2) INFORMATION FOR SEQ ID NO:10:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:10:

```
Met Arg Val Pro Ala Gln Leu Leu Gly Leu Leu Leu Leu Trp Leu Pro
  1               5                  10                  15

Gly Ala Arg Cys Glu Ser Val Leu Thr Gln Pro Pro Ser Val Ser Gly
             20                  25                  30

Ala Pro Gly Gln Lys Val Thr Ile Ser Cys Thr Gly Ser Thr Ser Asn
         35                  40                  45

Ile Gly Gly Tyr Asp Leu His Trp Tyr Gln Gln Leu Pro Gly Thr Ala
     50                  55                  60

Pro Lys Leu Leu Ile Tyr Asp Ile Asn Lys Arg Pro Ser Gly Ile Ser
 65                  70                  75                  80

Asp Arg Phe Ser Gly Ser Lys Ser Gly Thr Ala Ala Ser Leu Ala Ile
                 85                  90                  95

Thr Gly Leu Gln Thr Glu Asp Gly Ala Asp Tyr Tyr Cys Gln Ser Tyr
            100                 105                 110

Asp Ser Ser Leu Asn Ala Gln Val Phe Gly Gly Gly Thr Arg Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160
```

```
Ser Asp Phe Tyr Pro Gly Ala Val Thr Val Ala Trp Lys Ala Asp Ser
                165                 170                 175

Ser Pro Val Lys Ala Gly Val Glu Thr Thr Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
        210                 215                 220

Thr Val Glu Lys Thr Val Ala Pro Thr Glu Cys Ser
225                 230                 235
```

(2) INFORMATION FOR SEQ ID NO:11:

(i) SEQUENCE CHARACTERISTICS:
        (A) LENGTH: 1430 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..1431

(ix) FEATURE:
        (A) NAME/KEY: mat_peptide
        (B) LOCATION: 1..1431

(xi) SEQUENCE DESCRIPTION: SEQ ID NO:11:

```
ATG AAA CAC CTG TGG TTC TTC CTC CTG CTG GTG GCA GCT CCC AGA TGG       48
Met Lys His Leu Trp Phe Phe Leu Leu Leu Val Ala Ala Pro Arg Trp
 1               5                  10                  15

GTC CTG TCC CAG GTG CAG CTG CAG GAG TCG GGC CCA GGA CTG GTG AAG       96
Val Leu Ser Gln Val Gln Leu Gln Glu Ser Gly Pro Gly Leu Val Lys
             20                  25                  30

CCT TCG GAG ACC CTG TCC CTC ACC TGC GCT GTC TCT GGT GGC TCC ATC      144
Pro Ser Glu Thr Leu Ser Leu Thr Cys Ala Val Ser Gly Gly Ser Ile
         35                  40                  45

AGC GGT GGT TAT GGC TGG GGC TGG ATC CGC CAG CCC CCA GGG AAG GGG      192
Ser Gly Gly Tyr Gly Trp Gly Trp Ile Arg Gln Pro Pro Gly Lys Gly
     50                  55                  60

CTG GAG TGG ATT GGG AGT TTC TAT AGT AGT AGT GGG AAC ACC TAC TAC      240
Leu Glu Trp Ile Gly Ser Phe Tyr Ser Ser Ser Gly Asn Thr Tyr Tyr
 65                  70                  75                  80

AAC CCC TCC CTC AAG AGT CAA GTC ACC ATT TCA ACA GAC ACG TCC AAG      288
Asn Pro Ser Leu Lys Ser Gln Val Thr Ile Ser Thr Asp Thr Ser Lys
                 85                  90                  95

AAC CAG TTC TCC CTG AAG CTG AAC TCT ATG ACC GCC GCG GAC ACG GCC      336
Asn Gln Phe Ser Leu Lys Leu Asn Ser Met Thr Ala Ala Asp Thr Ala
            100                 105                 110

GTG TAT TAC TGT GTG AGA GAT CGT CTT TTT TCA GTT GTT GGA ATG GTT      384
Val Tyr Tyr Cys Val Arg Asp Arg Leu Phe Ser Val Val Gly Met Val
        115                 120                 125

TAC AAC AAC TGG TTC GAT GTC TGG GGC CCG GGA GTC CTG GTC ACC GTC      432
Tyr Asn Asn Trp Phe Asp Val Trp Gly Pro Gly Val Leu Val Thr Val
    130                 135                 140

TCC TCA GCT AGC ACC AAG GGC CCA TCG GTC TTC CCC CTG GCA CCC TCC      480
Ser Ser Ala Ser Thr Lys Gly Pro Ser Val Phe Pro Leu Ala Pro Ser
145                 150                 155                 160

TCC AAG AGC ACC TCT GGG GGC ACA GCG GCC CTG GGC TGC CTG GTC AAG      528
Ser Lys Ser Thr Ser Gly Gly Thr Ala Ala Leu Gly Cys Leu Val Lys
                165                 170                 175
```

```
GAC TAC TTC CCC GAA CCG GTG ACG GTG TCG TGG AAC TCA GGC GCC CTG      576
Asp Tyr Phe Pro Glu Pro Val Thr Val Ser Trp Asn Ser Gly Ala Leu
            180                 185                 190

ACC AGC GGC GTG CAC ACC TTC CCG GCT GTC CTA CAG TCC TCA GGA CTC      624
Thr Ser Gly Val His Thr Phe Pro Ala Val Leu Gln Ser Ser Gly Leu
            195                 200                 205

TAC TCC CTC AGC AGC GTG GTG ACC GTG CCC TCC AGC AGC TTG GGC ACC      672
Tyr Ser Leu Ser Ser Val Val Thr Val Pro Ser Ser Ser Leu Gly Thr
        210                 215                 220

CAG ACC TAC ATC TGC AAC GTG AAT CAC AAG CCC AGC AAC ACC AAG GTG      720
Gln Thr Tyr Ile Cys Asn Val Asn His Lys Pro Ser Asn Thr Lys Val
225             230                 235                 240

GAC AAG AAA GCA GAG CCC AAA TCT TGT GAC AAA ACT CAC ACA TGC CCA      768
Asp Lys Lys Ala Glu Pro Lys Ser Cys Asp Lys Thr His Thr Cys Pro
                245                 250                 255

CCG TGC CCA GCA CCT GAA CTC CTG GGG GGA CCG TCA GTC TTC CTC TTC      816
Pro Cys Pro Ala Pro Glu Leu Leu Gly Gly Pro Ser Val Phe Leu Phe
            260                 265                 270

CCC CCA AAA CCC AAG GAC ACC CTC ATG ATC TCC CGG ACC CCT GAG GTC      864
Pro Pro Lys Pro Lys Asp Thr Leu Met Ile Ser Arg Thr Pro Glu Val
        275                 280                 285

ACA TGC GTG GTG GTG GAC GTG AGC CAC GAA GAC CCT GAG GTC AAG TTC      912
Thr Cys Val Val Val Asp Val Ser His Glu Asp Pro Glu Val Lys Phe
        290                 295                 300

AAC TGG TAC GTG GAC GGC GTG GAG GTG CAT AAT GCC AAG ACA AAG CCG      960
Asn Trp Tyr Val Asp Gly Val Glu Val His Asn Ala Lys Thr Lys Pro
305             310                 315                 320

CGG GAG GAG CAG TAC AAC AGC ACG TAC CGT GTG GTC AGC GTC CTC ACC     1008
Arg Glu Glu Gln Tyr Asn Ser Thr Tyr Arg Val Val Ser Val Leu Thr
                325                 330                 335

GTC CTG CAC CAG GAC TGG CTG AAT GGC AAG GAG TAC AAG TGC AAG GTC     1056
Val Leu His Gln Asp Trp Leu Asn Gly Lys Glu Tyr Lys Cys Lys Val
            340                 345                 350

TCC AAC AAA GCC CTC CCA GCC CCC ATC GAG AAA ACC ATC TCC AAA GCC     1104
Ser Asn Lys Ala Leu Pro Ala Pro Ile Glu Lys Thr Ile Ser Lys Ala
        355                 360                 365

AAA GGG CAG CCC CGA GAA CCA CAG GTG TAC ACC CTG CCC CCA TCC CGG     1152
Lys Gly Gln Pro Arg Glu Pro Gln Val Tyr Thr Leu Pro Pro Ser Arg
    370                 375                 380

GAT GAG CTG ACC AAG AAC CAG GTC AGC CTG ACC TGC CTG GTC AAA GGC     1200
Asp Glu Leu Thr Lys Asn Gln Val Ser Leu Thr Cys Leu Val Lys Gly
385                 390                 395                 400

TTC TAT CCC AGC GAC ATC GCC GTG GAG TGG GAG AGC AAT GGG CAG CCG     1248
Phe Tyr Pro Ser Asp Ile Ala Val Glu Trp Glu Ser Asn Gly Gln Pro
                405                 410                 415

GAG AAC AAC TAC AAG ACC ACG CCT CCC GTG CTG GAC TCC GAC GGC TCC     1296
Glu Asn Asn Tyr Lys Thr Thr Pro Pro Val Leu Asp Ser Asp Gly Ser
            420                 425                 430

TTC TTC CTC TAC AGC AAG CTC ACC GTG GAC AAG AGC AGG TGG CAG CAG     1344
Phe Phe Leu Tyr Ser Lys Leu Thr Val Asp Lys Ser Arg Trp Gln Gln
        435                 440                 445

GGG AAC GTC TTC TCA TGC TCC GTG ATG CAT GAG GCT CTG CAC AAC CAC     1392
Gly Asn Val Phe Ser Cys Ser Val Met His Glu Ala Leu His Asn His
    450                 455                 460

TAC ACG CAG AAG AGC CTC TCC CTG TCT CCG GGT AAA TGA                 1431
Tyr Thr Gln Lys Ser Leu Ser Leu Ser Pro Gly Lys
465                 470                 475

(2) INFORMATION FOR SEQ ID NO:12:
```

(i) SEQUENCE CHARACTERISTICS:
    (A) LENGTH: 476 amino acids
    (B) TYPE: amino acid
    (D) TOPOLOGY: linear (ii) MOLECULE TYPE: protein (xi) SEQUENCE DESCRIPTION: SEQ ID NO:12:

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Ala Val Ser Gly Gly Ser Ile
         35                  40                  45

Ser Gly Gly Tyr Gly Trp Gly Trp Ile Arg Gln Pro Pro Gly Lys Gly
     50                  55                  60

Leu Glu Trp Ile Gly Ser Phe Tyr Ser Ser Gly Asn Thr Tyr Tyr
 65                  70                  75                  80

Asn Pro Ser Leu Lys Ser Gln Val Thr Ile Ser Thr Asp Thr Ser Lys
                 85                  90                  95

Asn Gln Phe Ser Leu Lys Leu Asn Ser Met Thr Ala Ala Asp Thr Ala
            100                 105                 110

Val Tyr Tyr Cys Val Arg Asp Arg Leu Phe Ser Val Val Gly Met Val
        115                 120                 125

Tyr Asn Asn Trp Phe Asp Val Trp Gly Pro Gly Val Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Ala Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365
```

```
                                     -continued

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475
```